(12) United States Patent
Miyawaki et al.

(10) Patent No.: US 9,490,433 B2
(45) Date of Patent: Nov. 8, 2016

(54) BENZOTHIENOBENZOTHIOPHENE DERIVATIVE, ORGANIC SEMICONDUCTOR MATERIAL, AND ORGANIC TRANSISTOR

(71) Applicants: DIC Corporation, Tokyo (JP); TOKYO INSTITUTE OF TECHNOLOGY, Tokyo (JP)

(72) Inventors: Atsuhisa Miyawaki, Sakura-shi (JP); Tetsuo Kusumoto, Kitaadachi-gun (JP); Yoshio Aoki, Kitaadachi-gun (JP); Aya Ishizuka, Sakura-shi (JP); Yoshinobu Sakurai, Sakura-shi (JP); Yasuyuki Watanabe, Sakura-shi (JP); Jun-ichi Hanna, Tokyo (JP)

(73) Assignees: DIC CORPORATION, Tokyo (JP); TOKYO INSTITUTE OF TECHNOLOGY, Tokyo (JP)

( * ) Notice: Subject to any disclaimer, the term of this patent is extended or adjusted under 35 U.S.C. 154(b) by 9 days.

(21) Appl. No.: 14/426,862

(22) PCT Filed: Sep. 10, 2013

(86) PCT No.: PCT/JP2013/074364
§ 371 (c)(1),
(2) Date: Mar. 9, 2015

(87) PCT Pub. No.: WO2014/038708
PCT Pub. Date: Mar. 13, 2014

(65) Prior Publication Data
US 2015/0228913 A1    Aug. 13, 2015

(30) Foreign Application Priority Data
Sep. 10, 2012 (JP) .................. 2012-198415

(51) Int. Cl.
H01L 51/00 (2006.01)
H01L 29/786 (2006.01)
C07D 495/04 (2006.01)
H01L 51/05 (2006.01)

(52) U.S. Cl.
CPC ......... *H01L 51/0074* (2013.01); *C07D 495/04* (2013.01); *H01L 29/786* (2013.01); *H01L 51/0052* (2013.01); *H01L 51/0067* (2013.01); *H01L 51/0068* (2013.01); *H01L 51/0558* (2013.01)

(58) Field of Classification Search
CPC ........... H01L 51/0074; H01L 51/0052; H01L 51/0067; H01L 29/786; H01L 51/0068; H01L 51/0558; C07D 495/04
See application file for complete search history.

(56) References Cited

U.S. PATENT DOCUMENTS

| 2011/0031487 A1 | 2/2011 | Saito et al. |
| 2011/0040107 A1 | 2/2011 | Goto et al. |
| 2012/0161109 A1 | 6/2012 | Wigglesworth et al. |
| 2014/0081028 A1 | 3/2014 | Hanna et al. |
| 2014/0128983 A1 | 5/2014 | Flaherty et al. |

FOREIGN PATENT DOCUMENTS

| JP | 2008-010541 A | 1/2008 |
| JP | 2009-073780 A | 4/2009 |
| JP | 2009-275032 A | 11/2009 |
| JP | 2009-286781 A | 12/2009 |
| JP | 2010-177644 A | 8/2010 |
| JP | 2011-241331 A | 12/2011 |
| JP | 2012-001442 A | 1/2012 |
| JP | 2012-134482 A | 7/2012 |
| WO | 2006/077888 A1 | 7/2006 |
| WO | 2008/047896 A1 | 4/2008 |
| WO | 2009/125704 A1 | 10/2009 |
| WO | 2009/125721 A1 | 10/2009 |
| WO | 2012/121393 A1 | 9/2012 |

OTHER PUBLICATIONS

International Search Report dated Oct. 8, 2013, issued in corresponding application No. PCT/JP2013/074364.

Primary Examiner — Samantha Shterengarts
Assistant Examiner — Matt Mauro
(74) Attorney, Agent, or Firm — Westerman, Hattori, Daniels & Adrian, LLP

(57) ABSTRACT

The present invention, the present invention relates to an organic semiconductor material having a benzothienobenzothiophene skeleton, an organic semiconductor ink containing the organic semiconductor material, and an organic transistor using the organic semiconductor material. An object of the present invention is to provide an organic semiconductor material that easily provides a film having a high carrier mobility without the need for a complicated process. It was found that a BTBT derivative having a particular arylene acetylene structure is crystallized by way of a high-order liquid crystal phase having a highly ordered molecular arrangement, and thus the BTBT derivative easily forms a film having a high mobility without requiring complicated heat treatment even when the film is formed by printing. This finding led to the achievement of the object.

7 Claims, 8 Drawing Sheets

(a)　　　　　　　　　　　(b)

(a)　　　　　　　　　　　(b)

(a)　　　　　　　　　　　(b)

(a) (b)

(a) (b)

(a) (b)

(a)

(b)

(a)

(b)

(a)

(b)

(a)  (b)

(a)  (b)

(a)  (b)

US 9,490,433 B2

BENZOTHIENOBENZOTHIOPHENE DERIVATIVE, ORGANIC SEMICONDUCTOR MATERIAL, AND ORGANIC TRANSISTOR

TECHNICAL FIELD

The present invention relates to a benzothienobenzothiophene derivative, an organic semiconductor material using the same, an organic semiconductor ink containing the same, and an organic transistor using the same.

BACKGROUND ART

Hitherto, thin-film transistors (TFTs) formed by using amorphous silicon, or polycrystalline silicon have been widely used as switching elements of a liquid crystal display device, an organic electroluminescence (EL) display device and the like. However, chemical vapor deposition (CVD) apparatuses used for producing such TFTs using silicon are expensive. Thus, the production of large TFT elements results in an increase in the production cost. In addition, since silicon materials are deposited at high temperatures, in view of a problem of heat resistance, these materials cannot be applied to plastic substrates, which are likely candidates for substrates of flexible displays in the future. To solve this problem, organic TFTs have been proposed in which, instead of a silicon semiconductor, an organic semiconductor is used in a channel semiconductor layer.

By preparing a solution of an organic semiconductor, a film of the organic semiconductor can be formed by printing at a low temperature. Accordingly, organic semiconductors do not require large-scale manufacturing facilities, and can also be applied to plastics, which have poor heat resistance. Thus, organic semiconductors are expected to take the lead in flexible displays. On the other hand, organic semiconductors have a problem in practical application in that carrier mobilities of organic semiconductors are lower than those of silicon semiconductors, resulting in a decreased response speed of TFTs. Recently however, organic semiconductors having mobilities equivalent to that of amorphous silicon have been developed.

For example, PTL 1 describes a compound having a 2,7-substituted[1]benzothieno[3,2-b][1]benzothiophene skeleton (hereinafter, [1]benzothieno[3,2-b][1]benzothiophene is abbreviated as "BTBT"). PTL 1 describes compounds having, as the substituents, substituents selected from halogens, $C_1$-$C_{18}$ alkyls, $C_1$-$C_{18}$ alkyls having halogens, $C_1$-$C_{18}$ alkyloxys, $C_1$-$C_{18}$ alkylthios, aryls, and aryls having at least one selected from halogens, $C_1$-$C_{18}$ alkyls, $C_1$-$C_{18}$ alkyls having halogens, $C_1$-$C_{18}$ alkyloxys, and $C_1$-$C_{18}$ alkylthios. It is described that the mobility ($cm^2$/Vs) of these compounds is 0.17 to 0.31 $cm^2$/Vs.

PTL 2 describes a compound having a 2,7-substituted BTBT skeleton. PTL 2 describes compounds having, as the substituents, substituents selected from a hydrogen atom and halogeno-substituted $C_1$-$C_{36}$ aliphatic hydrocarbon groups. It is described that the mobility ($cm^2$/Vs) of these compounds is 0.12 to 4.5 $cm^2$/Vs.

PTL 3 describes a compound having a 2,7-substituted BTBT skeleton having a chalcogenophene ring. It has been reported that adhesiveness between a semiconductor thin film and an electrode and thin-film stability in the air were improved by introducing a chalcogenophene ring, and that the mobility was 0.08 to 0.22 $cm^2$/Vs.

Furthermore, PTL 4 to PTL 6 describe compounds having a benzothienothiophene skeleton having an acetylene structure. It is described that these compounds are useful as a precursor of an organic semiconductor material and a precursor of an organic semiconductor polymer.

PTL 7 describes compounds that have various BTBT Skeletons and exhibit a high-order liquid crystal phase. However, derivatives according to the present invention are not known.

PTL 8 describes a compound for an organic thin-film transistor, the compound having a structure including an aromatic heterocyclic ring as a skeleton. However, derivatives according to the present invention are not described. According to the description of Examples, the order of the field-effect mobility is about $10^{-1}$ to $10^{-2}$ ($cm^2$/Vs).

PTL 9 describes that a specific organic compound having, at the center, an aromatic hydrocarbon group or an aromatic heterocyclic group and an acetylene structure can be used in an organic thin-film transistor. However, it is not described whether or not the compound exhibits a high-order liquid crystal phase, which is an object of the present invention.

As described above, many organic semiconductor materials having an improved mobility have been reported. However, in the case where an organic semiconductor thin film is formed by printing, it is difficult to obtain an organic semiconductor film having a high mobility because the organic semiconductor molecules are arranged randomly at the time of printing, and thus a flow path through which carriers flow is not formed. Accordingly, in this application, an organic semiconductor material that provides a film in which organic semiconductor molecules are easily oriented in one direction at the time of film formation by printing and through which carriers easily flow is required.

CITATION LIST

Patent Literature

PTL 1: International Publication No. WO 2006-077388
PTL 2: International Publication No. WO 2008-47896
PTL 3: Japanese Unexamined Patent Application Publication No. 2009-73780
PTL 4: Japanese Unexamined Patent Application Publication No. 2012-134482
PTL 5: Japanese Unexamined Patent Application Publication No. 2003-286781
PTL 6: Japanese Unexamined Patent Application Publication No. 2012-1442
PTL 7: International Publication No. WO 2012-121393
PTL 8: International Publication No. WO 2009-125704
PTL 9: International Publication No. WO 2009-125721

SUMMARY OF INVENTION

Technical Problem

However, many existing materials have a mobility of less than 1 $cm^2$/Vs, which is insufficient to drive liquid crystal display devices and organic EL devices. Although the compounds described in PTL 2, which have been reported to have high mobilities, can be formed into a film by spin coating, heat treatment must be performed in order for such compounds to exhibit high mobilities. Consequently, even in TFTs produced under the same conditions, the variation in mobility is increased by the variations in treatment temperature and treatment time.

Accordingly, organic semiconductor materials require, in addition to an improvement in the carrier mobility of the molecules thereof, a property whereby, even when a film is formed by printing, the performance does not decrease and a film having a high mobility is easily formed.

Accordingly, an object of the present invention is to provide an organic semiconductor material which easily provides a film having a high carrier mobility without the need for a complicated process and in which the variation in mobility of the resulting semiconductor element is small, and a compound which can be used as the organic semiconductor material.

Solution to Problem

In the present invention, as a result of intensive studies, it was found that a BTBT derivative having a particular arylene acetylene structure is crystallized by way of a high-order liquid crystal phase having a highly ordered molecular arrangement, and thus the BTBT derivative easily forms a film which has a high mobility and in which the variation in mobility is small without requiring complicated heat treatment even when the film is formed by printing. This finding resulted in the completion of the present invention.

Advantageous Effects of Invention

According to the present invention, an organic semiconductor having a high mobility and good performance stability in a TFT can be provided.

DESCRIPTION OF EMBODIMENTS

Figure 1:
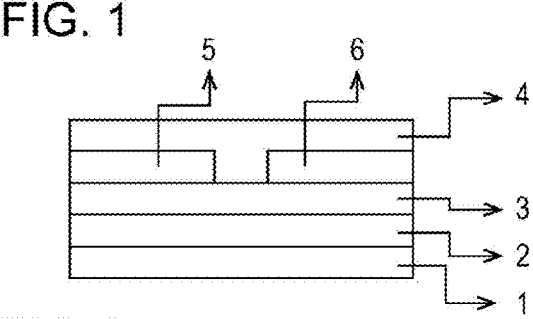
FIG. 1 is a schematic cross-sectional view of a bottom-contact-type transistor.

Specifically, the present invention is constituted by the following items.

1. A benzothienobenzothiophene derivative represented by general formula (1).

[Chem. 1]

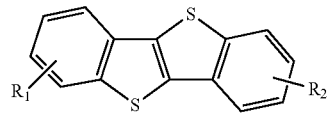

(I)

(in the formula, $R_1$— and $R_2$— are each (I) or (II) below, and at least one of $R_1$— and $R_2$— is (I).

(I) A group represented by general formula (2) or (3):

[Chem. 2]

(2)

[Chem. 3]

(3)

(where $Ar_1$ represents an aromatic hydrocarbon group or heteroaromatic group which may have a substituent, $Ar_2$ represents an aromatic hydrocarbon group which may have a substituent or a heteroaromatic group which may have a substituent, and R' represents a hydrogen atom, a trialkylsilyl group having an alkyl group having 1 to 4 carbon atoms, an alkyl group having 1 to 20 carbon atoms, or an aromatic hydrocarbon group or heteroaromatic group which may have a substituent.)

(II) A group selected from an alkyl group having 2 to 20 carbon atoms, an alkenyl group having 2 to 20 carbon atoms, an alkyl group having a halogen atom and 2 to 20 carbon atoms, an alkoxyalkyl group having 3 to 20 carbon atoms, an alkylsulfanylalkyl group having 3 to 20 carbon atoms, an alkylaminoalkyl group having 3 to 20 carbon atoms, an aromatic hydrocarbon group or heteroaromatic group, and an aromatic hydrocarbon group or heteroaromatic group having, as a substituent, an alkyl group having 1 to 20 carbon atoms, an alkenyl group having 2 to 20 carbon atoms, an alkyl group having a halogen atom and 1 to 20 carbon atoms, an alkoxyalkyl group having 3 to 20 carbon atoms, an alkylsulfanylalkyl group having 3 to 20 carbon atoms, or an alkylaminoalkyl group having 3 to 20 carbon atoms.)

2. The benzothienobenzothiophene derivative according to item 1, represented by general formula (4) below.

[Chem. 4]

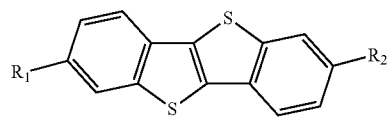

(4)

(In the formula, $R_1$— is a group represented by general formula (2) or (3) below:

[Chem. 5]

(2)

[Chem. 6]

(3)

(where $Ar_1$, $Ar_2$, and R' represent the same as the above, and $R_2$— is a group selected from an alkyl group having 2 to 20 carbon atoms, an alkenyl group having 2 to 20 carbon atoms, an alkyl group having a halogen atom and 2 to 20 carbon atoms, an alkoxyalkyl group having 3 to 20 carbon atoms, an alkylsulfanylalkyl group having 3 to 20 carbon atoms, an alkylaminoalkyl group having 3 to 20 carbon atoms, an aromatic hydrocarbon group or heteroaromatic group, and an aromatic hydrocarbon group or heteroaromatic group having, as a substituent, an alkyl group having 1 to 20 carbon atoms, an alkenyl group having 2 to 20 carbon atoms, an alkyl group having a halogen atom and 1 to 20 carbon atoms, an alkoxyalkyl group having 3 to 20 carbon atoms, an alkylsulfanylalkyl group having 3 to 20 carbon atoms, or an alkylaminoalkyl group having 3 to 20 carbon atoms.)

3. An organic semiconductor material using the benzothienobenzothiophene derivative according to item 1 or 2.

4. An organic semiconductor ink containing the organic semiconductor material according to item 3.

5. An organic semiconductor film containing the organic semiconductor material according to item 3.

6. An organic semiconductor device produced by using the organic semiconductor material according to item 3.

7. An organic transistor including the organic semiconductor material according to item 3 as an organic semiconductor layer.

(Compound Represented by General Formula (1))

The compound represented by general formula (1) is a compound having a BTBT skeleton having substituents, and characterized in that at least one of the substituents is a group which comprises a particular arylene acetylene structure, or is represented by general formula (2) or (3), and the other is a group selected from an alkyl group having 2 to 20 carbon atoms, an alkenyl group having 2 to 20 carbon atoms, an alkyl group having a halogen atom and 2 to 20 carbon atoms, an alkoxyalkyl group having 3 to 20 carbon atoms, an alkylsulfanylalkyl group having 3 to 20 carbon atoms, an alkylaminoalkyl group having 3 to 20 carbon atoms, an aromatic hydrocarbon group or heteroaromatic group, an aromatic hydrocarbon group or heteroaromatic group having, as a substituent, an alkyl group having 2 to 20 carbon atoms or an alkenyl group having 2 to 20 carbon atoms, an aromatic hydrocarbon group or heteroaromatic group having, as a substituent, an alkyl group having a halogen atom and 2 to 20 carbon atoms, an aromatic hydrocarbon group or heteroaromatic group having, as a substituent, an alkoxyalkyl group having 3 to 20 carbon atoms, an aromatic hydrocarbon group or heteroaromatic group having, as a substituent, an alkylsulfanylalkyl group having 3 to 20 carbon atoms, and an aromatic hydrocarbon group or heteroaromatic group having, as a substituent, an alkylaminoalkyl group having 3 to 20 carbon atoms, and a group represented by general formula (2) or (3).

In the organic semiconductor material of the present invention, a BTBT ring is connected to an aromatic ring with an acetylene site therebetween. This structure contributes to an improvement in the mobility due to the extension of the π-conjugated plane and the exhibition of a high-order liquid crystal phase due to the suppression of a rotational movement of the BTBT ring and the substituents. Thus, a semiconductor element which has a high mobility and in which the variation in mobility is small can be realized.

(List of Substituent of BTBT)

At least one of $R_1$ and $R_2$ of the compound represented by general formula (1) of the present invention is (I) a substituent represented by general formula (2) or general formula (3).

[Chem. 7]

$$Ar_1 \equiv \qquad (2)$$

[Chem. 8]

$$R' \equiv Ar_2 - \qquad (3)$$

$Ar_1$ of the substituent represented by general formula (2) is not particularly limited as long as $Ar_1$ is an aromatic hydrocarbon group which may have a substituent or a heteroaromatic group which may have a substituent. For example, $Ar_1$ may be any of the following groups.

Examples of the aromatic hydrocarbon group which may have a substituent include unsubstituted monocyclic or polycyclic aromatic hydrocarbon groups having 6 to 24 carbon atoms, such as a phenyl group, a naphthyl group, an azulenyl group, an acenaphthenyl group, an anthranyl group, a phenanthryl group, a naphthacenyl group, a fluorenyl group, a pyrenyl group, a chrysenyl group, a perylenyl group, a biphenyl group, a p-terphenyl group, and a quaterphenyl group;

alkyl-substituted aromatic hydrocarbon groups in which any of the aromatic hydrocarbon groups is substituted with an alkyl group having 1 to 18 carbon atoms, such as o-tolyl group, a m-tolyl group, a p-tolyl group, a 2,4-xylyl group, a 2,6-xylyl group, a mesityl group, a duryl group, a 4-ethylphenyl group, a 4-n-propylphenyl group, a 4-isopropylphenyl group, a 4-n-butylphenyl group, a 4-n-pentyl phenyl group, a 4-n-hexylphenyl group, a 4-n-decaphenyl group, a 4-stearylphenyl group, and a 9,9'-dihexylfluorenyl group;

alkenyl-substituted aromatic hydrocarbon groups in which any of the aromatic hydrocarbon groups is substituted with, an alkenyl group having 2 to 20 carbon atoms, such as a styryl group, a 4-butenylphenyl group, and a 4-octadecenylphenyl group;

halogenated aromatic hydrocarbon groups in which any of the aromatic hydrocarbon groups is substituted with a halogen, e.g., a fluorine atom, a chlorine atom, or a bromine atom, such as a 4-fluorophenyl group, a 2,6-fluorophenyl group, a 4-chlorophenyl group, and a 2,3,4, 5,6-perfluorophenyl group; alkoxyalkyl-substituted aromatic hydrocarbon groups in which any of the aromatic hydrocarbon groups is substituted with an alkoxyalkyl group having 3 to 20 carbon atoms, such as a 4-(2-ethoxyethyl)phenyl group, a 4-(2-n-hexyloxyethyl)phenyl group, a 4-(2-n-heptyloxyethyl)phenyl group, a 4-(2-n-tetradecyloxyethyl)phenyl group, a 4-(2-cyclohexyloxyethyl)phenyl group, a 4-(12-ethoxydodecyl)phenyl group, and a 4-(cyclohexyloxyethyl)phenyl group; alkylsulfanylalkyl-substituted aromatic hydrocarbon groups in which any of the aromatic hydrocarbon groups is substituted, with an alkylsulfanylalkyl group having 3 to 20 carbon atoms, such as a 4-(methyl sulfanylpropyl)phenyl group, a 4-(2-n-hexylsulfanylethyl)phenyl group, a 4-(3-n-decylsulfanylpropyl)phenyl group, and a 4-(cyclohexylsulfanylpropyl)phenyl group; and alkylaminoalkyl-substituted aromatic hydrocarbon groups in which any of the aromatic hydrocarbon groups is substituted with an alkylaminoalkyl group having 3 to 20 carbon atoms, such as a 4-(3-octylaminopropyl)phenyl group, a 4-(3-dodecylaminopropyl)phenyl group, and a 4-(diethylaminoethyl)phenyl group.

Examples of the heteroaromatic group which may have a substituent include 5-membered or 6-membered heteroaromatic groups such as a pyrrolyl group, an indolyl group, a furyl group, a thienyl group, an imidasolyl group, a benzofuryl group, a triazolyl group, benzotriazolyl group, a benzothienyl group, a pyrazolyl group, an indolizinyl group, a quinolinyl group, an isoquinolinyl group, a carbazolyl group, a dibenzofuranyl group, a dibenzotniophenyl group, an indolinyl group, a thiazolyl group, a pyridyl group, a pyrimidyl group, a pyrazinyl group, a pyridazinyl group, a thiadiazinyl group, an oxadiazolyl group, a benzoquinolinyl group, a thiadiazolyl group, a pyrrolothiazolyl group, a pyrrolopyridazinyl group, a tetrazolyl group, and an oxazolyl group, and polycyclic heteroaromatic groups in which benzene is fused, to any of the heteroaromatic groups; alkyl-substituted heteroaromatic groups in which any of the heteroaromatic groups is substituted with an alkyl group having 1 to 20 carbon atoms, such as a 5-methylthienyl group, a 5-hexylthienyl group, a 5-decathienyl group, and a 5-stearylthienyl group;

halogenated heteroaromatic groups in which any of the heteroaromatic groups is substituted with a halogen, e.g., a fluorine atom, a chlorine atom, or a bromine atom, such as a fluoropyridinyl group and a fluoroindolyl group;

alkoxyalkyl-substituted heteroaromatic groups in which any of the aromatic hydrocarbon groups is substituted with an alkoxyalkyl group having 3 to 20 carbon atoms, such as a 5-(2-ethoxyethyl)thienyl group, a 5-(2-n-tetradecyloxyethyl)thienyl group, a 5-(2-cyclohexyloxyethyl)thienyl group, and a 5-(2-ethoxydodecyl)thienyl group;

alkylsulfanylalkyl-substituted heteroaromatic groups in which any of the aromatic hydrocarbon groups is substituted with an alkylsulfanylalkyl group having 3 to 20 carbon atoms, such as a 5-(methylsulfanylpropyl)thienyl group, a 5-(2-n-hexylsulfanylethyl)thienyl group, a 5-(3-n-decylsulfanylpropyl)thienyl group, and a 5-(cyclohexylsulfanylpropyl)thienyl group; and alkylaminoalkyl-substituted heteroaromatic groups in which any of the heteroaromatic groups is substituted with an alkylaminoalkyl group having 3 to 20 carbon atoms, such as a 5-(3-octylaminopropyl)thienyl group, a 5-(3-dodecylaminopropyl)thienyl group, and a 5-(diethylaminoethyl)thienyl group.

From the viewpoint of exhibiting a high-order liquid crystal phase and suppressing she variation in mobility due to the high-order liquid crystal phase, among the above groups, $Ar_1$ is preferably an aromatic hydrocarbon group or heteroaromatic group which has a substituent, and particularly preferably an aromatic hydrocarbon group or heteroaromatic group which has a substituent having 1 to 12 carbon atoms.

$Ar_2$ of the substituent represented by general formula (3) is not particularly limited as long as $Ar_2$ is an aromatic hydrocarbon group which may have a substituent or a heteroaromatic group which may have a substituent. For example, $Ar_2$ may be any of the following groups.

Examples thereof include monocyclic or polycyclic aromatic hydrocarbon groups having 6 to 24 carbon atoms, such as a phenylene group, a naphthylene group, an azulenylene group, an acenaphthenylene group, an anthrylene group, a phenanthrylene group, a naphthacenylene group, a fluorenylene group, a pyrenylene group, a chrysenylene group, a perylenylene group, a biphenylene group, a p-terphenylene group, and a quaterphenylene group;

alkyl-substituted aromatic hydrocarbon groups in which any of the aromatic hydrocarbon groups is substituted with an alkyl group having 1 to 10 carbon atoms, such as a tolylene group, a xylylene group, an ethylphenylene group, a propylphenylene group, a butylphenylene group, a methylnaphthylene group, and a 9,9'-dihexylfluorenylene group; and halogenated aromatic, hydrocarbon groups in which any of the aromatic hydrocarbon groups is substituted with a halogen, e.g., a fluorine atom, a chlorine atom, or a bromine atom, such as a fluorophenylene group, a chlorophenylene group, and a bromophenylene group.

Furthermore, heteroaromatic groups such as thienylene and pyridylene and heteroaromatic groups, and heteroaromatic groups which is substituted with a substituent may also be used.

R' of the substituent represented by general formula (3) is not particularly limited as long as R' is a hydrogen atom, a trialkylsilyl group having an alkyl group having 1 to 4 carbon atoms, an alkyl group having 1 to 20 carbon atoms, an aromatic hydrocarbon group or heteroaromatic group which may have a substituent. For example, R' may be any of the following groups.

Examples of the trialkylsilyl group having an alkyl group having 1 to 4 carbon atoms include a trimethylsilyl group, a triethylsilyl group, a tri-n-propylsilyl group, a tri-isopropylsilyl group, a tri-n-butylsilyl, and a tri-sec-butyl group.

Examples of the alkyl group having 1 to 20 carbon atoms include linear, branched, or cyclic alkyl groups such as a methyl group, an ethyl group, a n-propyl group, an isopropyl group, a n-butyl group, an isobutyl group, a n-pentyl group, an isopentyl group, a neopentyl group, a n-hexyl group, a 1-methylpentyl group, a 4-methyl-2-pentyl group, a 3,3-dimethylbutyl group, a 2-ethylbutyl group, a n-heptyl group, a 1-methylhexyl group, a cyclohexylmethyl group, a n-octyl group, a tert-octyl group, a 1-methylheptyl group, a 2-ethylhexyl group, a 2-propylpentyl group, a n-nonyl group, a 2,2-dimethylheptyl group, a 2,6-dimethyl-4-heptyl group, a 3,5,5-trimethylhexyl group, a n-decyl group, a n-undecyl group, a 1-methyldecyl group, a n-dodecyl group, a n-tridecyl group, a 1-hexylheptyl group, a n-tetradecyl group, a n-pentadecyl group, a n-hexadecyl group, a n-heptadecyl group, a n-octadecyl group, a n-eicosyl group, a cyclopentyl group, a cyclohexyl group, a 4-methylcyclohexyl group, a cycloheptyl group, and a cyclooctyl group.

Examples of the aromatic hydrocarbon group which may have a substituent include monocyclic or polycyclic aromatic hydrocarbon groups having 6 to 24 carbon atoms, such as a phenyl group, a naphthyl group, an azulenyl group, an acenaphthenyl group, an anthranyl group, a phenanthryl group, a naphthacenyl group, a fluorenyl group, a pyrenyl group, a chrysenyl group, a perylenyl group, a biphenyl group, a p-terphenyl group, and a quaterphenyl group;

alkyl-substituted aromatic hydrocarbon groups in which any of the aromatic hydrocarbon groups is substituted with an alkyl group having 1 to 18 carbon atoms, such as o-tolyl group, a m-tolyl group, a p-tolyl group, a 2,4-xylyl group, a 2,6-xylyl group, a mesityl group, a duryl group, a 4-ethylphenyl group, a 4-n-propylphenyl group, a 4-isopropylphenyl group, a 4-n-butylphenyl group, a 4-n-pentylphenyl group, a 4-n-hexylphenyl group, a 4-n-decaphenyl group, a 4-stearylphenyl group, and a 9,9'-dihexylfluorenyl group;

alkenyl-substituted aromatic hydrocarbon groups in which any of the aromatic hydrocarbon groups is substituted with an alkenyl group having 2 to 20 carbon atoms, such as a styryl group, a 4-butenylphenyl group, and a 4-octadecenylphenyl group;

halogenated aromatic hydrocarbon groups in which any of the aromatic hydrocarbon groups is substituted with a halogen, e.g., a fluorine atom, a chlorine atom, or a bromine atom, such as a 4-fluorophenyl group, a 2,6-fluorophenyl group, a 4-chlorophenyl group, and a 2,3,4,5,6-perfluorophenyl group; alkoxyalkyl-substituted aromatic hydrocarbon groups in which any of the aromatic hydrocarbon groups is substituted with an alkoxyalkyl group having 3 to 20 carbon atoms, such as a 4-(2-ethoxyethyl)phenyl group, a 4-(2-n-hexyloxyethyl)phenyl group, a 4-(2-n-heptyloxyethyl)phenyl group, a 4-(2-n-tetradecyloxyethyl)phenyl group, a 4-(2-oyclohexyloxyethyl)phenyl group, a 4-(12-ethoxydodecyl)phenyl group, and a 4-(cyclohexyloxyethyl)phenyl group;

alkylsulfanylalkyl-substituted aromatic hydrocarbon groups in which any of the aromatic hydrocarbon groups is substituted with an alkylsulfanylalkyl, group having 3 to 20 carbon atoms, such as a 4-(methylsulfanylpropyl)phenyl group, a 4-(2-n-hexylsulfanylethyl)phenyl group, a 4-(3-n-decylsulfanylpropyl)phenyl group, and a 4-(cyclohexylsulfanylpropyl)phenyl group; and alkylaminoalkyl-substituted aromatic hydrocarbon groups in which any of the aromatic hydrocarbon groups is substituted with an alkylaminoalkyl group having 3 to 20 cartoon atoms, such as a 4-(3-octylaminopropyl)phenyl group, a 4-(3-dodecylaminopropyl)phenyl group, and a 4-(diethylaminoethyl)phenyl group.

Examples of the heteroaromatic group which may have a substituent include 5-membered or 6-membered heteroaromatic groups such as a pyrrolyl group, an indolyl group, a furyl group, a thienyl group, an imidazolyl group, a benzofuryl group, a triazolyl group, benzotriazolyl group, a benzothienyl group, a pyrazolyl group, an indolizinyl group, a quinolinyl group, an isoquinolinyl group, a carbazolyl group, a dibenzofuranyl group, a dibenzothiophenyl group, an indolinyl group, a thiazolyl group, a pyridyl group, a pyrimidyl group, a pyrazinyl group, a pyridazinyl group, a thiadiazinyl group, an oxadiazolyl group, a benzoquinolinyl group, a thiadiazolyl group, a pyrrolothiazolyl group, a pyrrolopyridazinyl group, a tetrazolyl group, and an oxazolyl group, and polycyclic heteroaromatic groups in which benzene is fused to any of the heteroaromatic groups; alkyl-substituted heteroaromatic groups in which any of the heteroaromatic groups is substituted with an alkyl group having 1 to 20 carbon atoms, such as a 5-methylthienyl group, a 5-hexylthienyl group, a 5-decathienyl group, and a 5-stearylthienyl group;

halogenated heteroaromatic groups in which any of the heteroaromatic groups is substituted with a halogen, e.g., a fluorine atom, a chlorine atom, or a bromine atom, such as a fluoropyridinyl group and a fluoroindolyl group; alkoxyalkyl-substituted heteroaromatic groups in which any of the aromatic hydrocarbon groups is substituted with an alkoxyalkyl group having 3 to 20 carbon atoms, such as a 5-(2-ethoxyethyl)thienyl group, a 5-(2-n-tetradecyloxyethyl)thienyl group, a 5-(2-cyclohexyloxyethyl)thienyl group, and a 5-(12-ethoxydodecyl)thienyl group; alkylsulfanylalkyl-substituted heteroaromatic groups in which any of the aromatic hydrocarbon groups is substituted with an alkylsulfanylalkyl group having 3 to 20 carbon atoms, such as a 5-(methylsulfanylpropyl)thienyl group, a 5-(2-n-hexylsulfanylethyl)thienyl group, a 5-(3-n-decylsulfanylpropyl)thienyl group, and a 5-(cyclohexylsulfanylpropyl)thienyl group; and alkylaminoalkyl-substituted heteroaromatic groups in which any of the heteroaromatic groups is substituted with an alkylaminoalkyl group having 3 to 20 carbon atoms, such as a 5-(3-octylaminopropyl)thienyl group, a 5-(3-dodecylaminopropyl)thienyl group, and a 5-(diethylaminoethyl)thienyl group.

Next, the other one of $R_1$ or $R_2$ of the compound represented by general formula (1) of the present invention is (I) a substituent represented by general formula (2) or general formula (3) above, or (II) a group selected from an alkyl group having 2 to 20 carbon atoms, an alkenyl group having 2 to 20 carbon atoms, an alkyl group having a halogen atom and 2 to 20 carbon atoms, an alkoxyalkyl group having 3 to 20 carbon atoms, an alkylsulfanylalkyl group having 3 to 20 carbon atoms, an alkylaminoalkyl group having 3 to 20 carbon atoms, an aromatic hydrocarbon group or heteroaromatic group, an aromatic hydrocarbon group or heteroaromatic group having, as a substituent, an alkyl group having 2 to 20 carbon atoms or an alkenyl group having 2 to 20 carbon atoms, an aromatic hydrocarbon group or heteroaromatic group having, as a substituent, an alkyl group having a halogen atom and 2 to 20 carbon atoms, an aromatic hydrocarbon group or heteroaromatic group having, as a substituent, an alkoxyalkyl group having 3 to 20 carbon atoms, an aromatic hydrocarbon group or heteroaromatic group having, as a substituent, an alkylsulfanylalkyl group having 3 to 20 carbon atoms, and an aromatic hydrocarbon group or heteroaromatic group having, as a substituent, an alkylaminoalkyl group having 3 to 20 carbon atoms. Examples of (II) will be described.

Examples of the alkyl group having 2 to 20 carbon atoms include linear, branched, or cyclic alkyl groups such as an ethyl group, a n-propyl group, an isopropyl group, a n-butyl group, an isobutyl group, a n-pentyl group, an isopentyl group, a neopentyl group, a n-hexyl group, a 1-methylpentyl group, a 4-methyl-2-pentyl group, a 3,3-dimethylbutyl group, a 2-ethylbutyl group, a n-heptyl group, a 1-methylhexyl group, a cyclohexylmethyl group, a n-octyl group, a tert-octyl group, a 1-methylheptyl group, a 2-ethylhexyl group, a 2-propylpentyl group, a n-nonyl group, a 2,2-dimethylheptyl group, a 2,6-dimethyl-4-heptyl group, a 3,5,5-trimethylhexyl group, a n-decyl group, a n-undecyl group, a 1-methyldecyl group, a u-dodecyl group, a n-tridecyl group, a 1-hexylheptyl group, a n-tetradecyl group, a n-pentadecyl group, a n-hexadecyl group, a n-heptadecyl group, a n-octadecyl group, a n-eicosyl group, a cyclopentyl group, a cyclohexyl group, a 4-methylcyclohexyl group, a cycloheptyl group, and a cyclooctyl group.

Examples of the alkenyl group having 2 to 20 carbon atoms include linear, branched, or cyclic alkenyl groups such as a vinyl group, an allyl group, a butenyl group, a pentenyl group, a hexenyl group, a heptenyl group, an octenyl group, a decenyl group, a dodecenyl group, a tetradecenyl group, a hexadecenyl group, an octadecenyl group, a methylpentenyl group, cyclohexene, and 4-methyl cyclohexene.

Examples of the alkyl group having a halogen atom and 2 to 20 carbon atoms include alkyl groups in which some of hydrogen atoms of any of the alkyl groups having 2 to 20 carbon atoms are substituted with fluorine atoms, such as a 2,2,3,3,3-pentafluoropropyl group, a 2,2,3,3,4,4,4-heptafluorobutyl group, a 2,2,3,3,4,4,5,5,5-nonafluoropentyl group, a 2,2,3,3,4,4,5,5,6,6,6-undecafluorohexyl group, and a 2,2,3,3,4,4,5,5,6,6,7,8,8,8-pentadecafluorooctyl group.

Examples of the alkoxyalkyl group having 3 to 20 carbon atoms include linear, branched, or cyclic alkoxyalkyl groups such as a 2-methoxyethyl group, a 2-ethoxyethyl group, a 2-n-propoxyethyl group, a 2-isopropoxyethyl group, a 2-n-butoxyethyl group, a 2-n-hexyloxyethyl group, a 2-(2'-ethylbutyloxy)ethyl group, a 2-n-heptyloxyethyl group, a 2-n-octyloxyethyl group, a 2-(2'-ethylhexyloxy)ethyl group, a 2-n-decyloxyethyl group, a 2-n-dodecyloxyethyl group, a 2-n-tetradecyloxyethyl group, a 2-cyclohexyloxyethyl group, a 2-methoxypropyl group, a 3-methoxypropyl group, a 3-ethoxypropyl group, a 3-n-propoxypropyl group, a 3-isopropoxypropyl group, a 3-n-butoxypropyl group, a 3-pentyloxypropyl group, a 3-n-hexyloxypropyl group, a 3-(2-ethylbutoxy)propyl group, a 3-n-octyloxypropyl group, a 3-(2'-ethylhexyloxy)propyl group, a 3-n-decyloxypropyl group, a 3-n-dodecyloxypropyl group, a 3-n-tetradecyloxypropyl group, a 3-cyclohexyloxypropyl group, a 4-methoxybutyl group, a 4-ethoxybutyl group, a 4-n-propoxybutyl group, a 4-isopropoxybutyl group, a 4-n-butoxybutyl group, a 4-n-hexyloxybutyl group, a 4-n-octyloxybutyl group, a 4-n-decyloxybutyl group, a 4-n-dodecyloxybutyl group, a 5-methoxypentyl group, a 5-ethoxypentyl group, a 5-n-propoxypentyl group, a 5-n-pentyloxypentyl group, a 6-methoxyhexyl group, a 6-ethoxyhexyl group, a 6-isopropoxyhexyl group, a 6-n-butoxyhexyl group, a 6-n-hexyloxyhexyl group, a 6-n-decyloxyhexyl group, a 4-methoxycyclohexyl group, a 7-methoxyheptyl group, a 7-ethoxyheptyl group, a 7-isopropoxyheptyl group, a 8-methoxyoctyl group, a 8-ethoxyoctyl group, a 9-methoxynonyl group, a 9-ethoxynonyl group, a 10-methoxydecyl group, a 10-ethoxydecyl group, a 10-n-butoxydecyl group, a 11-methoxyundecyl group, a 12-methoxydodecyl group, a 12-ethoxydodecyl group, a 12-isopropoxydodecyl group, a 14-methoxytetradecyl group, a cyclohexyloxyethyl group, and a cyclobexyloxypropyl group.

Examples of the alkylsulfanylalkyl group having 2 to 20 carbon atoms include alkylsulfanylalkyl groups such as a methylsulfanylpropyl group, an ethylsulfanylpropyl group, a butylsulfanylpropyl group, and a dodecylsulfanylpropyl group; and linear, branched, or cyclic alkylsulfanylalkyl groups such as a 2-methylsulfanylethyl group, a 2-ethylsulfanylethyl group, a 2-n-propylsulfanylethyl group, a 2-isopropylsulfanylethyl group, a 2-n-butylsulfanylethyl group, a 2-n-hexylsulfanylethyl group, a 2-(2'-ethylbutylsulfanyl)ethyl group, a 2-n-heptylsulfanylethyl group, a 2-n-octylsulfanylethyl group, a 2-(2'-ethylhexylsulfanyl)ethyl group, a 2-n-decylsulfanylethyl group, a 2-n-dodecylsulfanylethyl group, a 2-n-tetradecylsulfanylethyl group, a 2-cyclohexylsulfanylethyl group, a 2-methylsulfanylpropyl group, a 3-methylsulfanylpropyl group, a 3-ethylsulfanylpropyl group, a 3-n-propylsulfanylpropyl group, a 3-isopropylsulfanylpropyl group, a 3-n-butylsulfanylpropyl group, a 3-n-pentylsulfanylpropyl group, a 3-n-hexylsulfanylpropyl group, a 3-(2'-ethylbutylsulfanyl)propyl group, a 3-n-octylsulfanylpropyl group, a 3-(2'-ethylhexylsulfanyl)propyl group, a 3-n-decylsulfanylpropyl group, a 3-n-dodecylsulfanylpropyl group, a 3-n-tetradecylsulfanylpropyl group, a 3-cyclohexylsulfanylpropyl group, a 4-methylsulfanylbutyl group, a 4-ethylsulfanylbutyl group, a 4-n-propylsulfanylbutyl group, a 4-isopropylsulfanylbutyl group, a 4-n-butylsulfanylbutyl group, a 4-n-hexylsulfanylbutyl group, a 4-n-octylsulfanylbutyl group, a 4-n-decylsulfanylbutyl group, a 4-n-dodecylsulfanylbutyl group, a 5-methylsulfanylpentyl group, a 5-ethylsulfanylpentyl group, a 5-n-propylsulfanylpentyl group, a 5-n-pentylsulfanylpentyl group, a 6-methylsulflanylhexyl group, a 6-ethylsulfanylhexyl group, a 6-isopropylsulfanylhexyl group, a 6-n-butylsulfanylhexyl group, a 6-n-hexylsulfanylhexyl group, a 6-n-decylsulfanylhexyl group, a 4-methylsulfanylcyclohexyl group, a 7-methylsulfanylheptyl group, a ethylsulfanylheptyl group, a 7-isopropylsulfanylheptyl group, a 8-methylsulfanyloctyl group, a 5-ethylsulfanyloctyl group, a 9-methylsulfanylnonyl group, a 9-ethylsulfanylnonyl group, a 10-methylsulfanyldecyl group, a 10-ethylsulfanyldecyl group, a 10-n-butylsulfanyldecyl group, a 11-methylsulfanylundecyl group, a 12-methylsulfanyldodecyl group, a 12-ethylsulfanyldodecyl group, a 12-isopropylsulfanyldodecyl group, a 14-methylsulfanyltetradecyl group, a cyclohexylsulfanylethyl group, and a cyclohexylsulfanylpropyl group.

Examples thereof further include a 6-n-propylsulfanylhexyl group, a 7-n-propylsulfanylheptyl group, a 8-n-propylsulfanyloctyl group, a 9-n-propylsulfanylnonyl group, a 10-n-propylsulfanyldecyl group, a 11-ethylsulfanylundecyl group, and a 11-n-propylsulfanylundecyl group.

Examples of the alkylaminoalkyl group having 3 to 20 carbon atoms include linear, branched, or cyclic N-alkylaminoalkyl groups such as an N-methylaminoethyl group, an N-ethylaminoethyl group, an N-n-propylaminoethyl group, an N-isopropylaminoethyl group, an N-n-butylaminoethyl group, an N-n-hexylaminoethyl group, an N-2-ethylbutylaminoethyl group, an N-n-heptylaminoethyl group, an N-n-octylaminoethyl group, an N-2-ethylhexylaminoethyl group, an N-n-decylaminoethyl group, an N-n-dodecylaminoethyl group, an N-n-tetradecylaminoethyl group, an N-cyclohexylaminoethyl group, an N-methylaminopropyl group, an N-methylaminopropyl group, an N-ethylaminopropyl group, an N-n-propylaminopropyl group, an N-isopropylaminopropyl group, an N-n-butylaminopropyl group, an N-n-pentylaminopropyl group, an N-n-hexylaminopropyl group, an N-2-ethylbutylaminopropyl group, an N-n-octylaminopropyl group, an N-2-ethylhexylaminopropyl group, an N-n-decylaminopropyl group, an N-n-dodecylaminopropyl group, an N-n-tetradecylaminopropyl group, an N-cyclohexylaminopropyl group, an N-methylaminobutyl group, an N-ethylaminobutyl group, an N-n-propylaminobutyl group, an N-isopropylaminobutyl group, an N-n-butylaminobutyl group, an N-n-hexylaminobutyl group, an N-n-octylaminobutyl group, an N-n-decylaminobutyl group, an N-n-dodecylaminobutyl group, an N-methylaminopentyl group, an N-ethylaminopentyl group, an N-n-propylaminopentyl group, an N-n-pentylaminopentyl group, an N-methylaminohexyl group, an N-ethylaminohexyl group, an N-isopropylaminohexyl group, an N-n-butylaminohexyl group, an N-n-hexylaminohexyl group, an N-n-decylaminohexyl group, an N-methylaminocyclohexyl group, an N-methylaminoheptyl group, an N-ethylaminoheptyl group, an N-isopropylaminoheptyl group, an N-methylaminooctyl group, an N-ethylaminooctyl group, an N-methylaminononyl group, an N-ethylaminononyl group, an N-methylaminodecyl group, an N-ethylaminodecyl group, an N-n-butylaminodecyl group, an N-methylaminoundecyl group, an N-methylaminododecyl group, an N-ethylaminododecyl group, an N-isopropylaminododecyl group, an N-methylaminotetradecyl group, an N-cyclohexylaminoethyl group, and an N-cyclohexylaminopropyl group.

Examples of the aromatic hydrocarbon group or the heteroaromatic group include a phenyl group, a naphthyl group, an azulenyl group, an acenaphthenyl group, an anthranyl group, a phenanthryl group, a naphthacenyl group, a fluorenyl group, a pyrenyl group, a chrysenyl group, a perylenyl group, a biphenyl group, a p-terphenyl group, and a quaterphenyl group; a pyrrolyl group, an indolyl group, a furyl group, a thienyl group, an imidazolyl group, a benzofuryl group, a triazolyl group, benzotriazolyl group, a benzothienyl group, a pyrazolyl group, an indolizinyl group, a quinolinyl group, an isoquinolinyl group, a carbazolyl group, a dibenzofuranyl group, a dibenzothiophenyl group, an indolinyl group, a thiazolyl group, a pyridyl group, a pyrimidyl group, a pyrazinyl group, a pyridazinyl group, a thiadiazinyl group, an oxadiazolyl group, a benzoquinolinyl group, a thiadlazolyl group, a pyrrolothiazolyl group, a pyrrolopyridazinyl group, a tetrazolyl group, and an oxazolyl group; and halogen-substituted aromatic hydrocarbon groups or heteroaromatic groups in which some of hydrogen atoms of any of the aromatic hydrocarbon groups or heteroaromatic groups are substituted with a fluorine atom, a chlorine atom, a bromine atom, or an iodine atom, such as a 2-fluorophenyl group, a 3-fluorophenyl group, a 4-fluorophenyl group, a 2-chlorophenyl group, a 3-chlorophenyl group, a 4-chlorophenyl group, a 4-bromophenyl group, a 3,5-difluorophenyl group, and a 2,3,4,5,6-pentafluorophenyl group.

Examples of the aromatic hydrocarbon group or heteroaromatic group having, as a substituent, an alkyl group having 2 to 20 carbon atoms or an alkenyl group having 2 to 20 carbon atoms include aromatic hydrocarbon groups or heteroaromatic groups in which any of the aromatic hydrocarbon groups or any of the heteroaromatic groups has, as a substituent, an alkyl group or alkenyl group having 2 to 20 carbon atoms, such as a 4-ethylphenyl group, a 4-n-propylphenyl group, a 4-isopropylphenyl group, a 4-n-butylphenyl group, a 4-n-pentylphenyl group, a 4-isopentylphenyl group, a 4-n-hexylphenyl group, a 4-cyclohexylphenyl group, a 4-n-octylphenyl group, a 4-n-nonylphenyl group, a 4-n-decylphenyl group, a 4-n-undecylphenyl group, a 4-n-dodecylphenyl group, a 4-n-tetradecylphenyl group, a 4-n-octadecylphenyl group, a 5-n-butyl-2-thienyl group, a 5-n-hexyl-2-thienyl group, a 5-n-octyl-2-thienyl group, a 5-n-decyl-2-thienyl group, and a 5-n-tridecyl-2-thienyl group.

Examples of the aromatic hydrocarbon group or heteroaromatic group having, as a substituent, an alkyl group having a halogen atom and 2 to 20 carbon atoms include aromatic hydrocarbon groups or heteroaromatic groups in which any of the aromatic hydrocarbon groups or any of the heteroaromatic groups has, as a substituent, an alkyl group having a halogen, atom and 2 to 20 carbon atoms, such as a 4-pentafluoropropylphenyl group, a 4-heptafluorobutylphenyl group, a 4-nonaflouropentylphenyl group, a 4-pentadecaflourooctylphenyl group, a 4-nonadecafluorodecylphenyl group, and a 5-nonafluoropentyl-2-thienyl group.

Examples of the aromatic hydrocarbon group or heteroaromatic group having, as a substituent, an alkoxyalkyl group having 3 to 20 carbon atoms include aromatic hydrocarbon groups or heteroaromatic groups in which any of the aromatic hydrocarbon groups or any of the heteroaromatic groups has, as a substituent, an alkoxyalkyl group having 3 to 20 carbon, atoms, such as a 4-(2-ethoxyethyl)phenyl group, a 4-(2-n-hexyloxyethyl)phenyl group, a 4-(2-n-octyloxyethyl)phenyl group, a 4-(3-n-octyloxypropyl)phenyl group, a 4-(3-n-tetradecyloxypropyl)phenyl group, a 4-(4-n-octyloxybutyl)phenyl group, a 4-(6-n-decyloxyhexyl)phenyl group, a 4-(10-n-butoxydecyl)phenyl group, and a 5-(2-n-hexyloxyethyl)-2-thienyl group.

Examples of the aromatic hydrocarbon group or heteroaromatic group having, as a substituent, an alkylsulfanylalkyl group having 3 to 20 carbon atoms include aromatic hydrocarbon groups or heteroaromatic groups in which any of the aromatic hydrocarbon groups or any of the heteroaromatic groups has, as a substituent, an alkylsulfanylalkyl group having 3 to 20 carbon atoms, such as a 4-methylsulfanylpropylphenyl group, a 4-butylsulfanylpropylphenyl group, a 4-dodecylsulfanylpropylphenyl group, and a 5-methylsulfanylpropyl-2-thienyl group.

Examples of the aromatic hydrocarbon group or heteroaromatic group having, as a substituent, an alkylaminoalkyl group having 3 to 20 carbon atoms include aromatic hydrocarbon groups or heteroaromatic groups in which any of the aromatic hydrocarbon groups or any of the heteroaromatic groups has, as a substituent, an alkylaminoalkyl group having 3 to 20 carbon atoms, such as an N-methylaminopropylphenyl group, an N-butylaminopropylphenyl group, an N-dodecylaminopropylphenyl group, and an N-methylaminopropyl-2-thienyl group.

Among the (II) above, an alkyl group having 2 to 20 carbon atoms, an alkoxyalkyl group having 3 to 20 carbon atoms, an alkylsulfanylalkyl group having 3 to 20 carbon atoms, an aromatic hydrocarbon group or heteroaromatic group having, as a substituent, an alkyl group having 2 to 20 carbon atoms or an alkenyl group having 2 to 20 carbon atoms, an aromatic hydrocarbon group or heteroaromatic group having, as a substituent, an alkoxyalkyl group having 3 to 20 carbon atoms, and an aromatic hydrocarbon group or heteroaromatic group having, as a substituent, an alkylsulfanylalkyl group having 3 to 20 carbon atoms are preferable because these groups provide a high mobility.

Furthermore, from the viewpoint of exhibiting a high-order liquid crystal phase and suppressing the variation in mobility, the (II) above is preferably an alkyl group having 2 to 20 carbon atoms, an alkoxyalkyl group having 3 to 20 carbon atoms, and an alkylsulfanylalkyl group having 3 to 20 carbon atoms, and particularly preferably an alkyl group having 4 to 18 carbon atoms, an alkoxyalkyl group having 4 to 18 carbon atoms, and an alkylsulfanylalkyl group having 4 to 18 carbon atoms.

Examples of specific compounds of the present invention having the substituents described above include the following compounds, but are not limited thereto.

[Chem. 9]

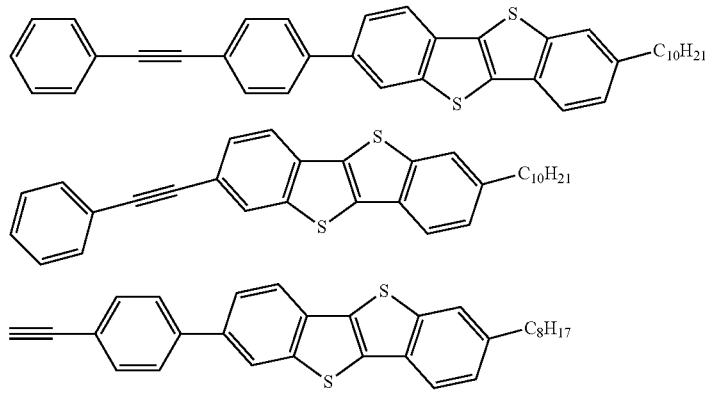

-continued
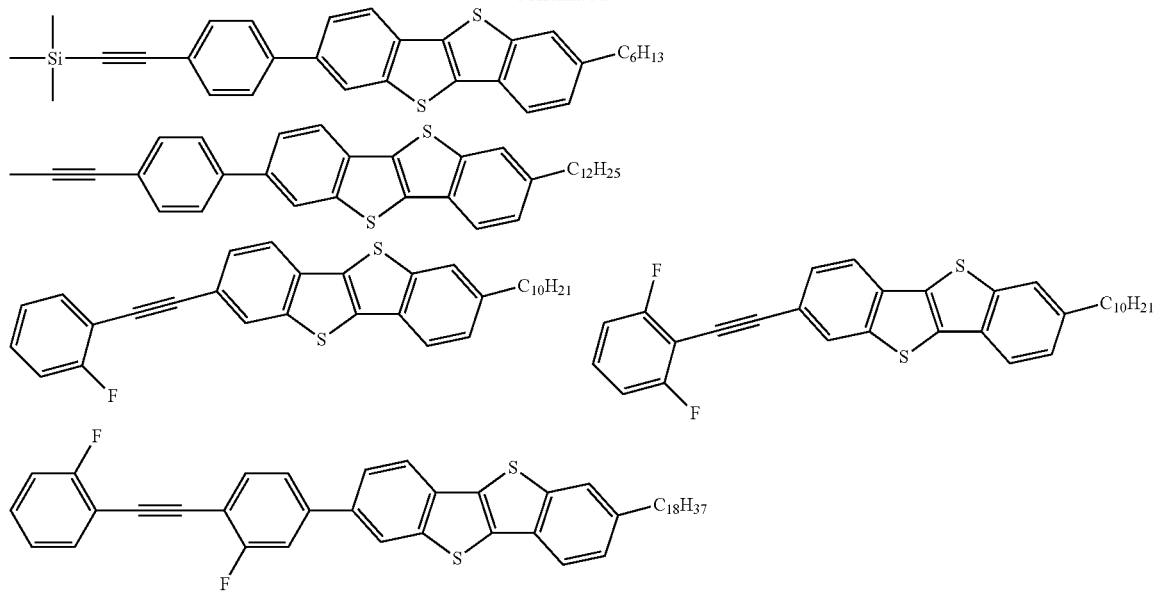
[Chem. 10]
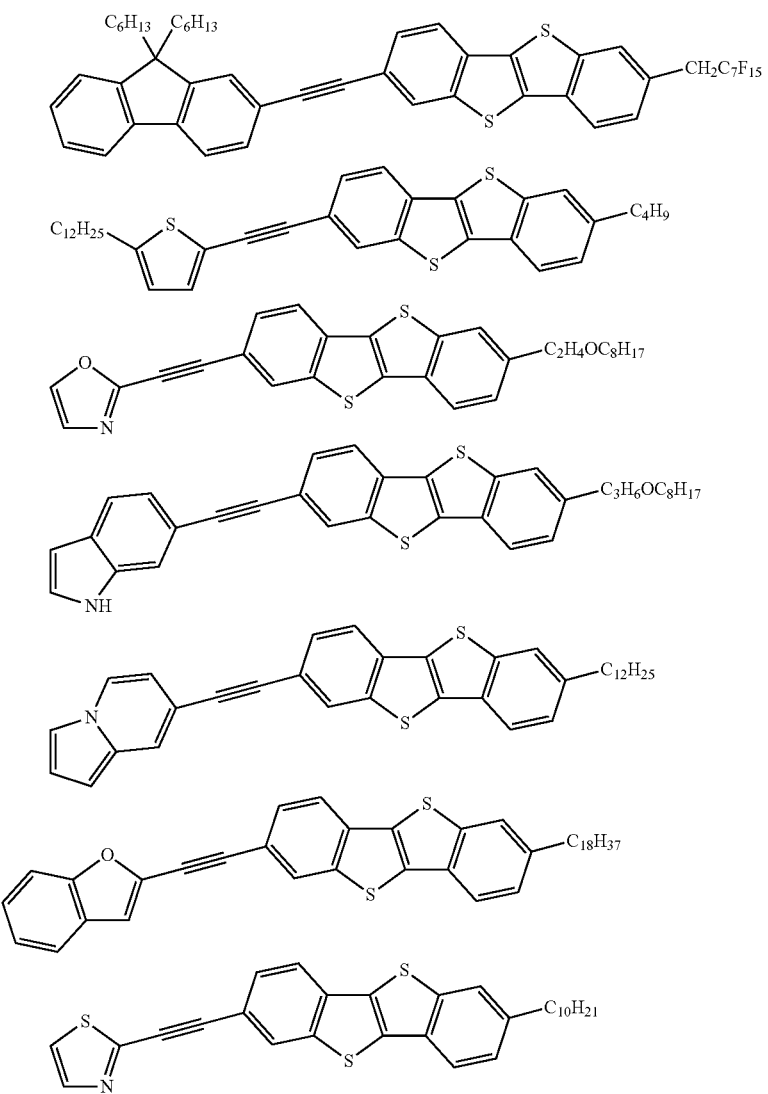

-continued
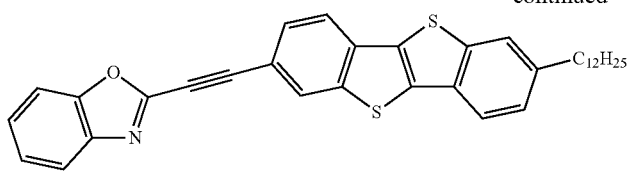
[Chem. 11]
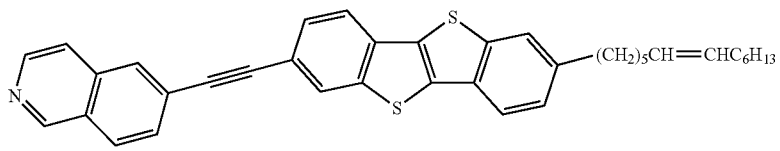
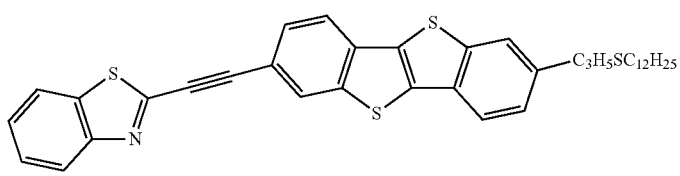
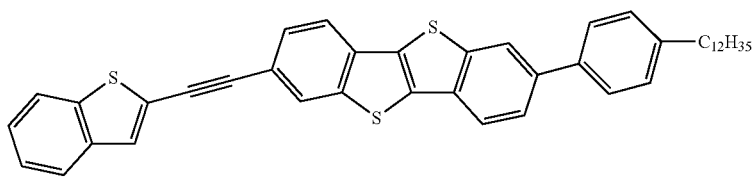
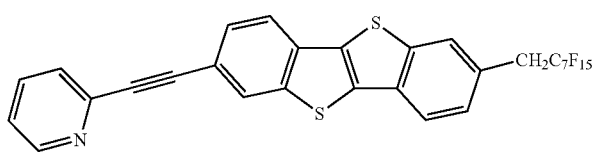
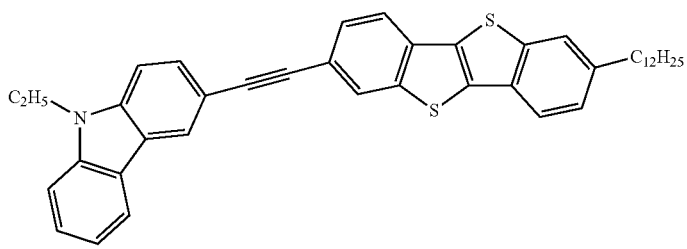
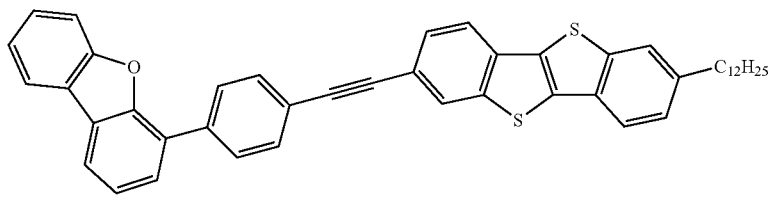
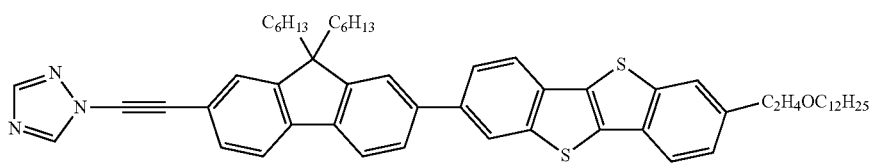
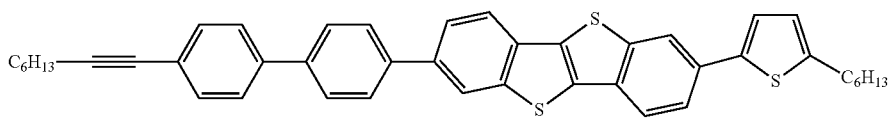

-continued
[Chem. 12]
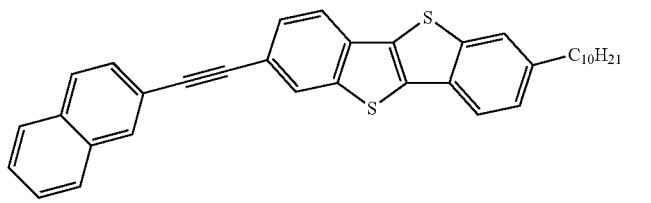
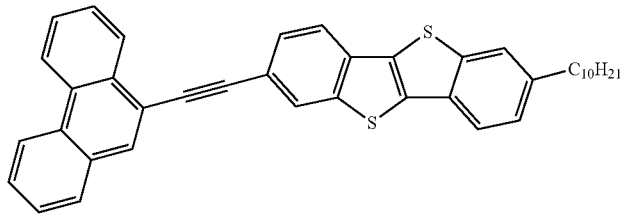
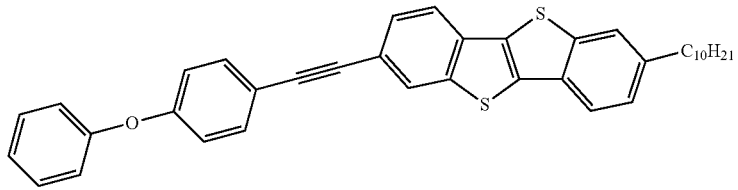
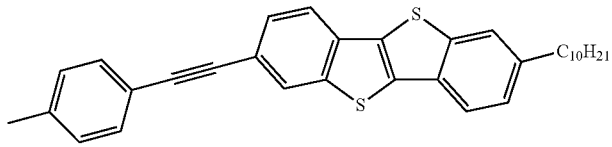
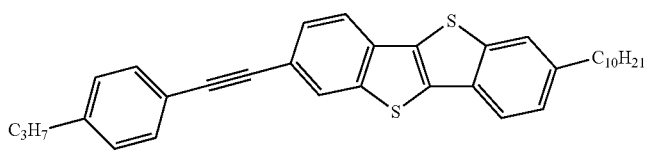
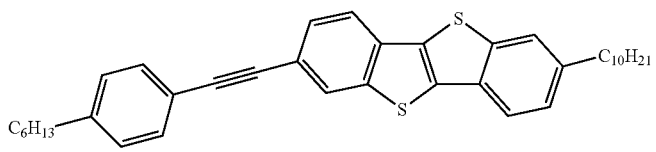
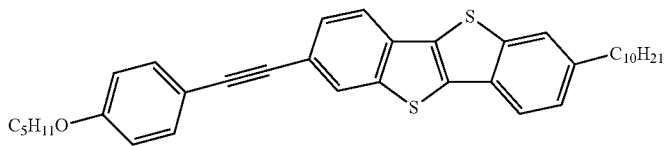
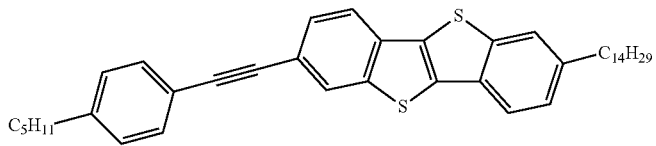
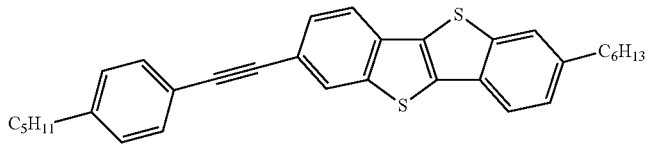
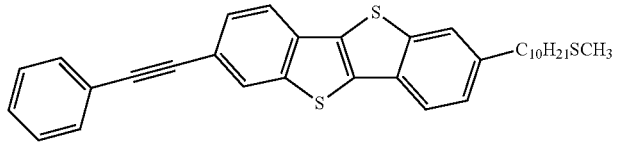

-continued

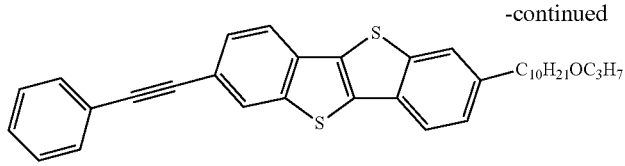

(Synthesis of Compound of the Present Invention)
A compound of the present, invention can be synthesized by using Known common methods in combination.
An example of the synthesis route is as follows.
(An Example of Synthesis Route)

[Chem. 13]

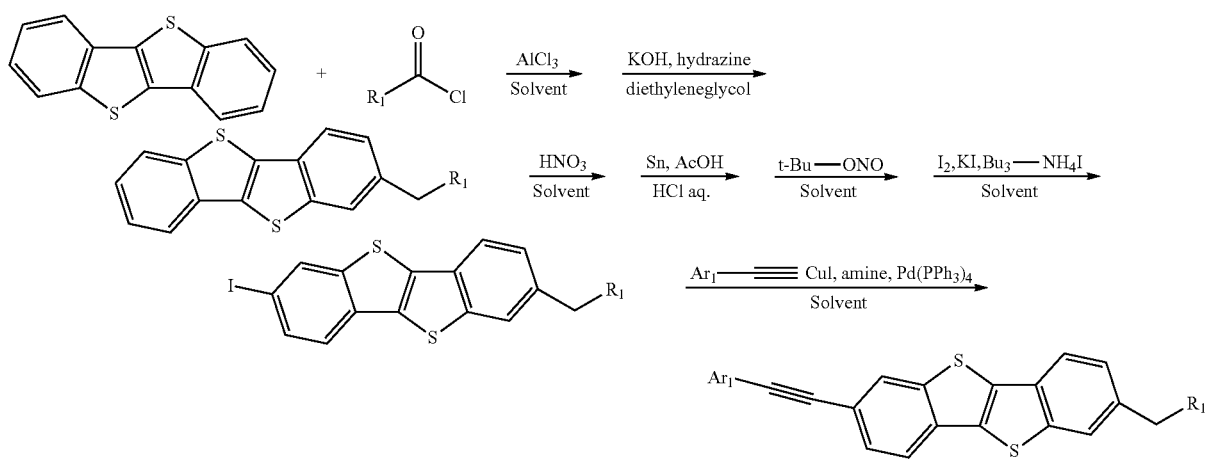

First, BTBT and an aliphatic carboxylic acid chloride are subjected to Friedel-Crafts acylation reaction, and then Wolff-Kishner reduction to obtain an alkylated compound. Next, a portion on the opposite side of the alkyl-substituted site is nitrated with fuming nitric acid, subsequently reduced to an amino group with a tin powder, subsequently subjected to diazotization with a nitrous acid compound, and further subjected to iodination by Sandmeyer reaction. Lastly, the resulting iodinated compound is subjected to Sonogashira coupling with an acetylene derivative. Thus, a target compound can foe obtained.

[Chem. 14]

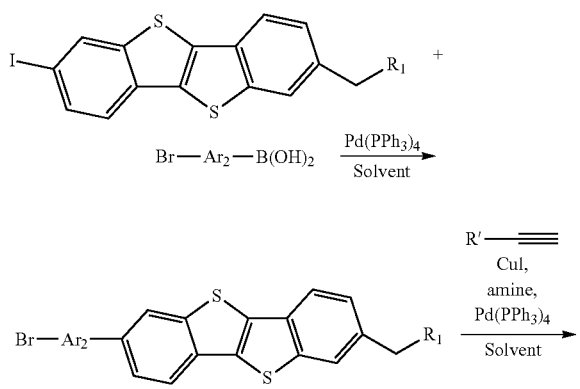

Alternatively, the iodinated BTBT compound obtained by the above reaction and an aromatic hydrocarbon compound having boric acid and bromine are allowed to react with each other by Suzuki-Miyaura coupling, and the resulting product is then subjected to Sonogashira coupling with an acetylene derivative. Thus, a target compound can be obtained.

The above reactions are not particularly limited. Known common reagents can be used. Any known common reaction temperature can also be used.

An organic semiconductor material of the present invention obtained as described, above is crystallized by way of a high-order liquid crystal phase having a highly ordered molecular arrangement, and the arrangement of the molecules of the organic semiconductor material is controlled after a film formation. Thus, the organic semiconductor material of the present invention exhibits a high charge mobility. In particular, since the organic semiconductor material has a carbon-carbon triple bond, which does not inhibit the liquid crystal phase and has a highly ordered molecular arrangement, the variation in mobility between elements is reduced compared with existing compounds. Accordingly, the organic semiconductor material, of the present invention is useful for various organic semiconductor devices.

(Liquid Crystal Phase)

A liquid crystal phase exhibited by the compound of the present invention is preferably a liquid crystal phase selected from the group consisting of SmB, $SmB_{cryst}$, SmI, SmF, SmE, SmJ, SmG, SmK, and SmH. The reason for this is as follows. In the case where the liquid crystal substance according to the present invention is used as an organic semiconductor in a liquid crystal phase, these liquid crystal phases have a low fluidity and thus do not easily induce ionic conduction, and these liquid crystal phases have a high order of molecular orientation and thus a high mobility can be expected in the liquid crystal phase. Furthermore, in the case where the liquid crystal substance according to the present invention is used as an organic semiconductor in a crystal phase, these liquid crystal phases have a lower fluidity than the N phase, SmA phase, and SmC phase, and thus breaking of the resulting element does not easily occur, even when the crystal phase transits to a liquid crystal phase as a result of an increase in the temperature. In the case where the exhibition of a liquid crystal phase is observed only in a temperature-decreasing process, once crystallization occurs, the crystal temperature range is extended, and thus this is advantageous when the liquid crystal substance is used in a crystal phase. The compound of the present invention is characterized by exhibiting a phase of $SmB_{cryst}$, SmE, SmF, SmI, SmJ, SmG, SmK or SmH in a temperature-decreasing process.

Furthermore, among these $SmB_{cryst}$, SmE, SmF, SmI, SmJ, SmG, SmK, and SmH, SmF, and SmG, which are higher-order Sm phases, are particularly preferable as a liquid crystal phase that appears in a temperature range adjacent to a liquid crystal phase when the temperature of the organic semiconductor material is increased from a crystal phase. In addition, in a liquid crystal substance in which, in addition to a low-order liquid crystal phase (such as the N phase, SmA phase, or SmC phase) having a strong liquid property, other high-order liquid crystal phase appears, since the low-order liquid crystal phase has a strong liquid property, the control of molecular orientation is easier than that in the high-order liquid crystal phase. Accordingly, molecules are oriented in advance in the low-order liquid crystal phase, and then allowed to transit to the high-order liquid crystal phase, thereby obtaining a liquid crystal thin film in which fluctuation of the molecular orientation and orientation defects are suppressed. Accordingly, an improvement in the quality of a liquid crystal thin film and a crystal thin film can be realized.

In the case where a liquid crystal substance is used as an organic semiconductor, the operating temperature desired for a device including the liquid crystal substance is usually −20° C. to 80° C. Accordingly, in the invention of the subject application, it is desirable that a temperature range in which the $SmB_{cryst}$, SmE, SmF, SmI, SmJ, SmG, SmK, or SmH phase appears be −20° C. or more. In addition, in the case where a liquid crystal substance according to the present invention is used as an organic semiconductor in a crystal phase, a thin film in the liquid crystal state (liquid crystal thin film) is preferably used as a precursor for the preparation of a crystal thin film from the viewpoint of improving the quality of the organic semiconductor. For this reason, in consideration of the simplicity of the process and the ease of the selection of the substrate, the temperature at which a liquid crystal phase of the liquid crystal substance appears is preferably 200° C. or less.

By using a molecular unit including an aromatic π-electron fused ring having a number of rings of 3 or more as a charge transporting molecular unit corresponding to a core part in a liquid crystal molecule, redundancy of the transfer integral with respect to fluctuation of the molecular position can be ensured. Similarly, by employing a molecular unit having a fused ring structure rather than a molecular unit including a π-electron conjugated system in which a plurality of benzenes, thiophenes, and the like are connected to each other with single bonds, the molecular conformation is fixed, and an increase in the transfer integral, can be expected, which is useful for an improvement in the mobility. Accordingly, the BTBT skeleton of the present invention is useful as the unit.

In contrast, even when a charge transporting molecular unit having a large fused ring structure is employed as a core part, in a substance in which a hydrocarbon, chain is directly connected to the core part as in, for example, dialkylpentacene or dialkylbenzothienobenzothiophene, stabilization of a liquid crystal phase is not achieved, and, in general, a liquid crystal phase is not exhibited, or even if a liquid crystal phase is exhibited, only a low-order liquid crystal phase such as SmA phase is exhibited (literature: Liquid Crystals, Vol. 34, No. 9 (2007) 1001-1007, Liquid Crystals, Vol. 30, No. 5 (2003) 603-610). Therefore, even if a large fused ring structure is merely used in a charge transporting molecular unit, a high mobility cannot be realized in a liquid crystal phase. Only when a molecular structure in which another structural unit for providing the degree of freedom of the flip-flop movement of a molecule is connected to the charge transporting molecular unit, such as the BTBT skeleton, is employed in the core part, exhibition of a high-order liquid crystal phase and realization of a high mobility in a liquid crystal phase can be expected.

A hydrocarbon chain may be connected to such a structure (core part) in which another rigid structural unit such as an arylene acetylene structure is connected to the BTBT skeleton so as to provide the molecule with anisotropy of the rod-like molecular shape and a liquid property. In this case, exhibition of a liquid crystal phase can be induced with high probability. In the case of connecting a hydrocarbon chain, in general, two hydrocarbon chains are connected to the core part. However, even when a single hydrocarbon chain is connected to the core part, a liquid crystal phase can be often exhibited. In this case, the temperature range in which the liquid crystal phase appears is often asymmetric between a temperature-increasing process and a temperature-decreasing process. This is useful in that a liquid crystal phase temperature range generally extends to a low temperature in the temperature-decreasing process, whereas a crystal phase extends to a high-temperature range in the temperature-increasing process. This property means that, in the case where a polycrystalline thin film of a liquid crystal substance is used as an organic semiconductor, when a polycrystalline thin film is prepared by using a liquid crystal thin film (thin film in a state of a liquid crystal phase) as a precursor thereof, the liquid crystal thin film can be prepared at a lower temperature, and is advantageous in that the process is more easily performed. In addition, the extension of the crystal phase temperature in the temperature-increasing process to the high-temperature range means that thermal stability of the prepared polycrystalline film improves, and this is advantageous as a material. On the other hand, when two hydrocarbon chains are provided, in general, the exhibited liquid crystal phase is stabilized. This is advantageous for applications to a device or the like using a liquid crystal phase.

In the case where a substance is synthesized on the basis of the basic molecular design described above, the usefulness of the substance relating to the present invention is achieved by selecting, fundamentally, a substance that exhibits a high-order smectic phase in the case where the substance is used as an organic semiconductor in a liquid crystal phase, and a substance in which, when cooled from a temperature higher than the crystal phase temperature, a crack or a void is not easily formed in a crystal thin film, and a low-order liquid crystal phase adjacent to the crystal phase is not exhibited in the case where the substance is used as an organic semiconductor in a crystal phase. In other words, the determination is made based on whether a liquid crystal phase other than a nematic phase, SmA phase, and SmC phase is exhibited in a temperature range adjacent to a crystal phase in the case where the substance is used as an organic semiconductor in a liquid crystal phase and whether a crack or a void is not easily formed when the substance is cooled from a temperature higher than the crystal phase temperature to allow the substance to transit to a crystal phase in the case where the substance is used as an organic semiconductor in a crystal phase.

(Screening Method of Liquid Crystal Phase)

The above determination can be easily made by a screening method (determination method described below. Regarding the details of measuring methods used in this screening method, the literature below may be referred to, as required.

Literature A:. How to use polarizing microscope: Jikken Kagaku Kouza (Experimental Chemistry course), Fourth edition, Vol. 1, Maruzen Co. Ltd., pp. 439 to 435

Literature B: Evaluation of liquid crystal material: Jikken Kagaku Kouza (Experimental Chemistry Course), Fifth edition, vol. 27, pp. 295 to 300, Maruzen Co. Ltd.

: Ekisho Kagaku Jikken Nyumon (Introduction of Liquid Crystal Science Experiments) Edited by The Japanese Liquid Crystal Society, SIGMA SHUPPAN (S1) After an isolated test substance is purified by column chromatography and recrystallization, it is confirmed by silica gel thin-layer chromatography that the test substance shows a single spot (that is, the test substance is not a mixture).

(S2) A sample heated to an isotropic phase is injected into a cell by using a capillary action, the cell having a thickness of 15 μm and being produced by bonding slide glasses to each other with a spacer therebetween. The cell is heated to an isotropic phase temperature and the texture of the isotropic phase is observed with a polarizing microscope to confirm that a dark field of view is not observed in a temperature range lower than the isotropic phase. This result shows that the molecular major axis is horizontally aligned with respect to a substrate, and becomes a requirement necessary for the subsequent texture observations.

(S3) The texture is observed with the microscope while cooling the cell at a suitable temperature-decreasing rate, for example, at a rate of about 5° C./min. In this case, if the cooling rate is excessively high, the structure to be formed becomes small, and a detailed observation becomes difficult. Therefore, the temperature is increased to the isotropic phase again, and the cooling rate is adjusted so as to determine conditions for obtaining a structure size of 50 μm or more, under which the structure can be easily observed.

(S4) The texture is observed under the conditions determined in the section (S3) above while cooling from the isotropic phase to room temperature (20° C.). During this process, when the sample is crystallized in the cell, a crack or a void is generated as a result of the contraction of the lattice, and a black line or a region having a certain size appears in the texture to be observed. It air enters during the injection of the sample, a similar black region (in general, circular region) is locally generated. However, since the black line or the region generated by the crystallization appears so as to be distributed in the structure or boundary, the black line or the region is easily distinguished. These black line and region can be easily discriminated from other structures observed in the texture because even when a polarizer and an analyzer are rotated, disappearance and a change in color are not observed. The temperature at which, this texture appears is defined as a crystallization temperature, and it is confirmed that a texture that appears in a temperature range higher than the crystallization temperature is not a nematic phase, SmA phase, or SmC phase. In the case where the sample exhibits a nematic phase, a characteristic Schlieren texture (typical Schlieren texture), which is expressed as a bobbin-like texture, is observed. In the case where the sample exhibits SmA phase or SmC phase, a characteristic texture (typical Fan-like texture), which is called "Fan-like texture" having a fan shape and having a uniform structure in the region, is observed. Accordingly, these phases can be easily determined from the characteristic textures thereof.

Regarding a particular case, in a substance that undergoes transition from SmA phase to SmB phase or from SmC phase to SmF or SmI phase, a change in the field of view may be momentarily observed at a phase transition temperature, however, a change in the texture after the phase transition may be hardly observed. Accordingly, a careful observation may foe required because the textures of the formed SmB phase, or SmF phase or SmI phase may be misidentified as SmA phase or SmC phase in some cases. In such a case, it is important to pay attention to a momentary change in the field of view, the change being observed at the phase transition temperature. In the case where this confirmation is necessary, the number of intermediate phases is determined by differential scanning calorimetry (DSC), X-ray diffraction is then measured at respective temperature ranges, and the presence or absence of a peak in a high-angle region (from 15 to 30 degrees in the determination of θ-2θ) characteristic of each phase is confirmed. Thus, the SmA phase and SmC phase (both of which have no peak) can easily be discriminated from the SmB phase, SmF phase, and SmI phase (each of which has a peak).

(S5) A substance in which a black structure is not observed by the texture observation with a polarizing microscope at room temperature (20° C.) can be used as an organic semiconductor material. Accordingly, regardless of a high-order liquid crystal phase or a crystal phase (including a metastable crystal phase) at room temperature, this substance is considered to be a substance in the scope of the present invention.

From the viewpoint of applying the organic semiconductor material according to the present invention to a device, the energy levels of the highest occupied molecular orbital (HOMO) and the lowest unoccupied molecular orbital (LUMO) of the core part are also important. In general, the HOMO level of an organic semiconductor can be estimated as follows. A test substance is dissolved in an organic solvent such as dehydrated dichloromethane so as to have a concentration of, for example, 1 to 10 mmol/L, and about 0.2 mol/L of a supporting electrolyte such as tetrabutylammonium salt is added thereto. A working electrode such as Pt, a counter electrode such as Pt, and a reference electrode such as Ag/AgCl are inserted into the resulting solution. A CV curve is then drawn by performing sweeping with a potentiostat at a rate of about 50 mV/sec. From the difference between the peak potential and a potential of a known substance such as ferrocene serving as a reference, the HOMO level and the LUMO level can be estimated. In the case where the HOMO level or the LUMO level deviates from the potential window of the organic solvent used, the HOMO level or the LUMO level can be estimated by calculating the HOMO-LUMO level from an absorption edge of an ultraviolet-visible absorption spectrum and subtracting the result from the level that has been measured. This method can be perforated, with reference to J. Pommerehne, H. Vestweber, W. Guss, R. F. Mahrt, H. Bassler, M. Porsch, and J. Daub, Adv. Mater., 7, 551 (1995).

In general, the HOMO and LUMO levels of an organic semiconductor material provide a standard of electrical contact with an anode and a cathode, respectively. An attention should be paid because the charge injection is limited by the magnitude of energy barrier determined by the difference from the work function of an electrode material. With regard to the work function of a metal, examples of the work function of substances that are often used as an electrode include silver (Ag): 4.0 eV, aluminum (Al): 4.28 eV, gold (Au): 5.1 eV, calcium (Ca): 2.87 eV, chromium (Cr): 4.5 eV, copper (Cu): 4.65 eV, magnesium (Mg): 3.66 eV, molybdenum (Mo): 4.6 eV, platinum (Pt): 5.65 eV, indium tin oxide (ITO): 4.35 to 4.75 eV, and sine oxide (SnO): 4.68 etc. From the viewpoint described above, the difference in the work function between the organic semiconductor material and the electrode substance is preferably 1 eV or less, more preferably 0.8 eV or less, and still more preferably 0.6 eV or less. Regarding the work function of a metal, the following literature may be referred to, as required. Literature D: Kagaku Binran (Handbook of Chemistry), Basic Edition, Revised 5th edition, II-608-610, 14.1 b Work Function (Maruzen Co. Ltd.) (2004)

The HOMO and LUMO energy levels are affected by the size of the conjugated π-electron system of the core part. Therefore, the size of the conjugated system is used as a reference when the material is selected. Furthermore, introduction of a hetero atom into the core part is effective as a method for changing the HOMO or LUMO energy level.

Examples of applicable organic semiconductor devices include diodes, organic transistors, memories, photodiodes, light-emitting diodes, light-emitting transistors, sensors such as a gas sensor, a biosensor, a blood sensor, an immunological sensor, an artificial retina, and a taste sensor, and radio frequency identifiers (RFIDs).

In particular, since the organic semiconductor material of the present invention has a high charge mobility of 0.1 cm$^2$/Vs or more, the organic semiconductor material is particularly useful to applications to an organic transistor or a light-emitting device. The organic transistor can be suitably used as a transistor for switching a pixel that forms a display, a signal driver circuit element, a memory circuit element, a signal processing circuit element, or the like. Examples of the display include a liquid crystal display, a dispersion-type liquid crystal display, an electrophoresis display, a particle-rotation-type display element, an electrochromic display, an organic electroluminescence display, and electronic paper.

In general, an organic transistor includes a source electrode, a drain electrode, a gate electrode, a gate insulating layer, and an organic semiconductor layer. There are various types of organic transistors depending on the arrangements of respective electrodes and respective layers. The organic semiconductor material of the present invention can be used in any transistor regardless of the type of the transistor. Regarding the type of transistors, for example, Fundamentals of material science Vol. 6 "Fundamental of Organic Transistor" published by Sigma-Aldrich Co., LLC may be referred to.

(With Regard to Mobility)

The mobility in the present invention refers to a mobility of a carrier such as a hole or an electron, and serves as an index that represents performance of an organic semiconductor material. With regard to the mobility, there are a mobility determined by a TOF (Time-of-Flight) method ($\mu^{TOF}$: unit cm$^2$/V·s) and a mobility determined by an organic transistor ($\mu^{FET}$: unit cm$^2$/V·s). The higher the $\mu^{TOF}$ or $\mu^{FET}$, the more easily a carrier flows.

The mobility ($\mu^{TOF}$) is determined by a formula (i) below where V represents a voltage between electrodes of a cell for measuring TOF, d represents a distance between the electrodes, and Tr represents a time during which & carrier passes through a film thickness calculated from a waveform of a photocurrent. The mobility ($\mu^{FET}$) is determined by a formula (ii) below using a transfer characteristic curve obtained by fixing a drain voltage $V_D$ and changing a gate voltage $V_G$.

[Math. 1]
$$\mu^{TOP} = d^2/(V/Tr) \qquad (i)$$

[Math. 2]
$$\sqrt{I_D} = \sqrt{\frac{\mu^{FET} \cdot C_{in} \cdot W}{2L}} (V_G - V_{TH}) \qquad (ii)$$

(In the formula (ii), $C_{in}$ represents an electric capacity per unit area of a gate insulating film, $I_D$ represents a drain current, L represents a channel length, W represents a channel width, and $V_{TH}$ represents a threshold voltage.)

When an organic semiconductor is applied to a device, the mobility exhibited by the substance serves as a standard of the usefulness. This is because characteristics of the device are limited by the mobility. The mobility of existing amorphous organic semiconductors is about 10$^{-2}$ cm$^2$/Vs even in a case of a high mobility, and is usually 10$^{-2}$ to 10$^{-3}$ cm$^2$/Vs. Accordingly, it is difficult for amorphous organic semiconductor materials to realize a high mobility exceeding 10$^{-2}$ cm$^2$/Vs exhibited by a liquid crystal phase, in particular, a mobility exceeding 0.1 cm$^2$/Vs exhibited by a high-order smectic phase. Thus, the superiority of liquid crystal materials is clear.

Liquid crystalline substances exhibit a crystal phase, similarly to non-liquid crystal substances. Therefore, when liquid crystal substances are used as organic semiconductors, the liquid crystal substances can be used as organic semiconductors not only in a liquid crystal phase but also in a crystal phase. In general, the mobility in a crystal phase is often higher than the mobility in a liquid crystal phase by approximately from half order to one order of magnitude. In particular, the use of a crystal phase is effective in applications to a transistor that requires a high mobility and applications to a solar cell or the like that requires a long diffusion length of an electric charge or an exciton.

(Confirmation of Semiconductor Device Operation)

As described in Examples, by producing an FET and evaluating the characteristics of the FET, it is possible to confirm that the organic semiconductor material of the present invention can be used as an organic transistor.

With regard to details of the confirmation of the semiconductor device operation by this method, for example, the literature of S. F. Nelsona, Y.-Y. Lin, D. J, Gundlach, and T. H. Jackson, Temperature-independent transport in high-mobility pentacene transistors, Appl. Phys. Lett., 72, No. 15, 1854-1856 (1998) may be referred to.

(Organic Semiconductor Ink)

The organic semiconductor material of the present invention may be subjected to vapor deposition to form a semiconductor film. However, the organic semiconductor material of the present invention is preferably used as a printing ink with which a film can be formed at a low temperature and which has good productivity. In the preparation of an ink, the organic semiconductor material of the present invention is dissolved in a solvent, and, in order to provide ink properties, a leveling agent such as a fluorine-based leveling agent or a silicon-based leveling agent, and a polymer compound, such as polystyrene or an acrylic resin, serving as a viscosity modifier may be added within a range where semiconductor performance is not impaired.

Any organic solvent may be used, and two or more organic solvents may be used as a mixture. Specific examples thereof include, but are not limited to, aliphatic solvents such as n-hexane, n-octane, n-decane, and n-dodecane; alicyclic solvents such as cyclohexane; aromatic solvents such as benzene, toluene, cumene, o-xylene, m-xylene, p-xylene, p-cymene, mesitylene, anisole, 2-methylanisole, 3-methylanisole, 4-methylanisole, 2,5-dimethylanisole, 3,5-dimethoxytoluene, 2,4-dimethylanisole, phenetole, methyl benzoate, ethyl benzoate, propyl benzoate, butyl benzoate, 1,5-dimethyltetralin, n-propyl benzene, n-butyl benzene, n-pentyl benzene, 1,3,5-triethylbenzene, 1,3-dimethoxybenzene, chlorobenzene, o-dichlorobenzene, and trichlorobenzene; ether solvents such as tetrahydrofuran, dioxane, ethylene glycol diethyl ether, anisole, benzyl ethyl ether, ethyl phenyl ether, diphenyl ether, and methyl-t-butyl ether; ester solvents such as methyl acetate, ethyl acetate, Ethyl Cellosolve, and propylene glycol methyl ether acetate; alcohol solvents such as methanol, ethanol, and isopropanol; ketone solvents such as acetone, methyl ethyl ketone, cyclohexanone, 2-hexanone, 2-heptanone, and 3-heptanone; dimethylformamide; dimethyl sulfoxide; and diethylformamide.

The concentration of the organic semiconductor material of the present invention in a prepared liquid composition is preferably 0.01% to 20% by weight, and more preferably 0.1% to 10% by weight.

The organic solvent may be used alone. In order to obtain a thin film having a desired high homogeneity, a plurality of solvents may be used as a mixture.

(Organic Transistor)

Next, an organic transistor that includes an organic semiconductor material of the present invention will be described.

In general, an organic transistor includes a source electrode, a drain electrode, a gate electrode, a gate insulating layer, and an organic semiconductor layer. There are various types of transistors depending on the arrangements of respective electrodes and respective layers. The organic semiconductor material of the present invention can be used in any transistor regardless of the type of the transistor. Regarding the types of transistors, for example, Fundamentals of material science Vol. 6 "Fundamental of Organic Transistor" published by Sigma-Aldrich Co., LLC may be referred to.

A detailed description will be made using a bottom contact-type transistor shown in FIG. 1 as an example. Reference numeral 1 denotes a substrate, reference numeral 2 denotes a gate electrode, reference numeral 3 denotes a gate insulating layer, reference numeral 4 denotes an organic semiconductor, reference numeral 5 denotes a source electrode, and reference numeral 6 denotes a drain electrode.

The substrate is constituted by glass or a flexible resin sheet. For example, a plastic film may be used as a sheet. Examples of the plastic film include films composed of polyethylene terephthalate (PET), polyethylene naphthalate (PEN), polyether sulfone (PES), polyetherimide, polyether ether ketone, polyphenylene sulfide, polyarylate, polyimide, polycarbonate (PC), cellulose triacetate (TAC), cellulose acetate propionate (CAP), or the like. By using a plastic film in this manner, a reduction in weight can be realized, portability can be enhanced, and the resistance to impact can be improve compared with the case where a glass substrate is used.

An electrode material of the gate electrode, the source electrode, or the drain electrode is not particularly limited to as long as the material is an electrically conductive material. Examples of the electrodes that are used include metal electrodes composed of platinum, gold, silver, nickel, chromium, copper, iron, tin, tin oxide/antimony, indium/tin oxide (ITO), sine oxide doped with fluorine, carbon, graphite, glassy carbon, silver paste and carbon paste, lithium, beryllium, sodium, magnesium, potassium, calcium, scandium, titanium, manganese, zirconium, gallium, niobium, sodium, a sodium-potassium alloy, magnesium, lithium, aluminum, a magnesium/copper mixture, a magnesium/silver mixture, a magnesium/aluminum mixture, a magnesium/indium mixture, an aluminum/aluminum oxide mixture, a lithium/aluminum mixture, or the like. Furthermore, known electrically conductive polymers in which the electrical conductivity is improved by doping or the like, for example, conductive polyaniline, conductive polypyrrole, conductive polythiophene, and a complex of polyethylenedioxythiophene and polystyrene sulfonic acid are also suitably used.

Examples of a method for forming an electrode include a method including forming a conductive thin film using the above material as a raw material by a method such as vapor deposition or sputtering, and forming an electrode using the conductive thin film by a known photolithographic method or lift-off method, and a method including etching a metal foil composed of aluminum, copper, or the like by using a resist formed on the metal foil by thermal transfer, ink-jetting, or the like. Alternatively, a solution or dispersion of an electrically conductive polymer, or a dispersion of electrically conductive fine particles may be directly patterned by ink-jetting. Alternatively, an electrode may be formed from a coating film by lithography, laser ablation, or the like. Furthermore, a method may also be used in which an ink, conductive paste, or the like that contains an electrically conductive polymer or electrically conductive fine particles is patterned by a printing method such as letterpress printing, intaglio printing, planographic printing, screen printing, or the like.

As the gate insulating layer, an organic thin film composed of a thermoplastic resin such as parylene, polystyrene, an acrylic resin, or a polyester resin; a thermosetting resin such as an epoxy resin, a urethane resin, a phenolic resin, an unsaturated polyester resin, an alkyd resin, or a melamine resin; or a UV-curable resin can be suitably used. Alternatively, an inorganic material such as a silicon oxide film may also be used.

The gate insulating layer may be formed by preparing a thin film using a known wet film forming method such as a Spin, coating method, a casting method, a dip method, an ink-jet method, a doctor blade method, a screen printing method, an off-set printing method, a letterpress printing method, a reverse printing method, a microcontact printing method, a wire bar coating method, a spray coating method, or a dispensing method. The thin film may be patterned to have a desired shape by a photolithographic method, as required.

The organic semiconductor layer can be produced by a known common production method such as a vacuum evaporation method. However, an ink for an organic semiconductor material may be prepared in the form of a composition, and the organic semiconductor layer can be easily formed by a printing method.

Examples of the printing method include a spin coating method, a casting method, a dip method, an ink-jet method, a doctor blade method, a gravure printing method, a screen printing method, an off-set printing method, a letterpress printing method, a reverse printing method, a microcontact printing method, a wire bar coating method, a spray coating method, and a dispensing method. A thin film can be prepared by such a known, wet film forming method. By using a casting method or the like, the form of a plate-shaped crystal or a thick film can also be obtained. An organic transistor of the present invention can be suitably used as a transistor for switching of a pixel that forms a display, a signal driver circuit element, a memory circuit element, a signal processing circuit element, or the like. Examples of the display include a liquid crystal display, a dispersion-type liquid crystal display, an electrophoresis display, a particle-rotation-type display element, an electrochromic display, an organic electroluminescence display, and electronic paper.

(Organic Semiconductor Device)

Examples of applicable organic semiconductor devices, include diodes, organic transistors, memories, photodiodes, light-emitting diodes, light-emitting transistor, sensors such as a gas sensor, a biosensor, a blood sensor, an immunological sensor, an artificial retina, and a taste sensor, and RFIDs.

EXAMPLES

The present invention will be described in more detail using Examples.

Observation of Liquid Crystal Phase

First, an organic semiconductor material was placed on a slide glass washed with ion exchange water and acetone in that order by using ultrasonic waves and then dried. A cover glass that had been similarly washed was placed thereon to prepare a specimen for measurement. The specimen was placed on an ECLIPSE E600 POL (eyepiece: 10 times, objective lens: 20 times) manufactured by Nikon Corporation and equipped with a hot stage (manufactured toy Mettler-Toledo International Inc., FP82HT), and was heated until the temperature reached a melting point at a temperature-increasing rate of 5° C./min. The melting of the organic semiconductor material was confirmed. While pressing the cover glass with tweezers, the organic semiconductor material was stretched so as to form a thin film.

Next, a phase change in a cooling process was observed with a polarizing microscope while cooling the specimen at a rate of 5° C./min. In each figure, part (a) shows a texture of a crystal phase, and part (b) shows a texture of a high-order liquid crystal phase.

<Preparation of Transistor>

A silicon wafer having a thermal oxidation film (heavily doped p-type silicon (P+-Si), thickness of thermal oxidation film ($SiO_2$): 300 nm) was cut to have a size of 20×25 mm. The cut silicon wafer (hereinafter abbreviated as "substrate") was then washed by using ultrasonic waves with a neutral detergent, ultrapure water, isopropyl alcohol (IPA), acetone, and IPA in that order.

Next, a liquid crystalline organic semiconductor compound was dissolved in xylene to prepare a solution. The concentration of the solution was adjusted to 1% to 0.5% by weight. This solution and a glass pipette for applying the solution onto the substrate were heated in advance on the hot stage to a predetermined temperature. The substrate was placed on a spin coater installed in an oven, and the temperature in the oven was increased to 60° C. Subsequently, the solution was applied onto the substrate, and the substrate was rotated (at about 3,000 rpm for 30 seconds). After the rotation was stopped, the substrate was rapidly taken out and cooled to room temperature. Furthermore, gold was deposited, through a metal mask, on the substrate having an organic semiconductor layer thereon by a vacuum deposition method ($2 \times 10^{-6}$ Torr) so as to have a pattern. Thus, source and drain, electrodes were formed (channel length:channel width=75 µm:3,000 µm). The prepared organic transistor was evaluated as follows. In a usual air atmosphere, a current flowing between the source electrode and the drain electrode was measured (transfer characteristic) by using a source-measurement unit having two power supplies while performing sweep application ($V_{sg}$: +40 to −60 V) of a voltage to the gate electrode (P+-Si) (voltage $V_{sd}$ between source electrode and drain electrode: −80 V). The mobility was calculated from the slope of $\sqrt{Id}$-Vg in the transfer characteristic by a well-known method using a formula of saturation characteristics.

The measurement of the mobility was performed for five transistors, and an average thereof was calculated. Furthermore, an error was calculated by determining a standard deviation of the measured values, and calculating from a formula "Error (%)=(standard deviation/average)×100".

Example 1

In 320 mL of dichloromethane, 4.96 g (13 mmol) of 2-decyl-BTBT prepared by the method described in Liquid Crystals 31, 137-1380 (2004) was dissolved, and the resulting solution was then cooled to −50° C. Subsequently, 24 mL of a 1.2 M dichloromethane solution of fuming nitric acid was added dropwise thereto over a period of 30 minutes. The resulting solution was further stirred at −50° C. for two hours, and 26 mL of a saturated aqueous solution of sodium hydrogencarbonate was then added thereto to terminate the reaction. The resulting liquid was separated, and the lower layer was collected. The lower layer was washed with a 10% saline solution, and dried with anhydrous magnesium sulfate. The resulting liquid was concentrated and dried to obtain a crude solid. The solid was recrystallized from 2-butanone to obtain 3.72 g of a yellow crystal of 2-decyl-7-nitro BTBT (yield 67%).

Subsequently, 2.56 g (6 mmol) of 2-decyl-7-nitro BTBT and 1.84 g of a tin powder were suspended in 30 mL of acetic acid, and 5.4 ml of concentrated hydrochloric acid was gradually added dropwise while heating at about 0° C. and stirring. Furthermore, the reaction was performed at 100° C. for one hour, and the reaction mixture was then cooled to 10° C. or less. A solid was collected by filtration.

The solid was dispersed in about 100 mL of chloroform, and washed with concentrated aqueous ammonia and a saturated saline solution in that order. The resulting dispersion was dried with anhydrous magnesium sulfate, and then concentrated and dried to obtain a crude solid. The solid was separated, and purified with a silica gel column (chloroform/cyclohexane=1:1, 1% triethylamine was added), and recrystallized from petroleum benzine to obtain 1.72 g of light gray 2-amino-7-decyl BTBT (yield 72%).

Furthermore, 60 mL of dichloromethane was added to 1.58 g (4 mmol) of 2-amino-decyl BTBT, and 864 mg of a trifluoroborate/ether complex and 504 mg of t-butyl nitrite were added dropwise to the solution under cooling at −15° C. The reaction temperature was increased to 5° C. over a period of about one hour. Subsequently, 12 mL of a solution of dichloromethane-tetrahydrofuran (THF) mixed solvent (1:2) containing 1.6 g of iodine, 1.32 g of potassium iodide, and 100 mg of tetrabutylammonium iodide was added thereto. A reaction was performed under reflux by heating for eight hours. The reaction mixture was then diluted with chloroform, and sequentially washed with 10% sodium thiosulfate, 5 M sodium hydroxide, and a 10% saline solution. The reaction mixture was dried with anhydrous sodium sulfate, and concentrated and dried. The resulting deep brown crude solid was purified with a silica gel column (chloroform/cyclohexane=1:1), and crystallized from chloroform-methanol. The resulting crystal was then recrystallized from ligroin to obtain 912 mg of 2-decyl-7-iodo BTBT (yield 45%).

Lastly, 8 mL of dioxane, 0.5 mL of 2 M tripotassium phosphate, and 183 mg (0.6 mmol, Aldrich) of 4-(phenylethyl)phenylboric acid pinacol ester were added to 253 mg (0.5 mmol) of 2-decyl-7-iodo BTBT, argon gas was bubbled for 20 minutes. Subsequently, 30 mg (0.025 mmol, Tokyo Chemical Industry Co., Ltd.) of tetrakis(triphenylphosphine) palladium and 13 mg (0.045 mmol, Wako Pure Chemical Industries, Ltd.) of tricyclohexylphosphine were added thereto, and resulting reaction mixture Was heated while stirring at 95° C. for 22 hours. The reaction mixture was diluted with chloroform, and washed with a 10% saline solution. The lower layer was concentrated and dried to obtain a crude solid. The solid was recrystallized from xylene to obtain 140 mg of BTBT derivative a represented by (Chem. 15) (yield 63%).

$^1$HNMR (300 MHz, CDCl$_3$): δ 8.12 (d, 1H, J=1.8 Hz, H-6), 7.92 (d, 1H, J=8.2 Hz, H-9), 7.79 (d, 1H, J=7.8 Hz, H-4), 7.73 (s, 1H, H-1), 7.69-7.53 (m, 9H, H-8, H-2', -3', -5', -6' of Ph, H-2', -3', -5', -6' of Ph), 7.29 (dd, 1H, J=7.8 Hz, H-3), 7.38 (tt, 1H, J=7.8 Hz, H-4' of Ph), 2.77 (t, 2H, J=7 Hz, BTBT-CH$_2$), 1.70 (quint. 2H, J=7 Hz, BTBT-CH$_2$CH$_2$), 1.55-1.27 (m, 14H, CH$_2$×7), 0.88 (t, 3H, J=7 Hz, CH$_3$).

FD-MS: [M]$^+$=556.3

[Chem. 15]

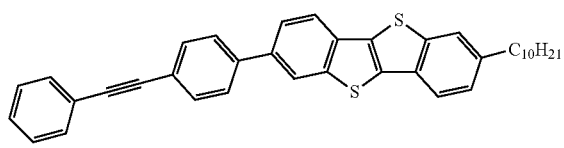

Example 2

Copper iodide (0.11 g, 0.6 mmol), bis(triphenylphosphine)palladium(II) dichloride (0.08 g, 0.1 mmol), and 36 mL of triethyl amine were added to 2-decyl-7-iodo BTBT (253 mg, 0.5 mmol) obtained in Example 1, and nitrogen gas was bubbled at room temperature for 15 minutes. Subsequently, 0.55 g (5.4 mmol) of ethynylbenzene was added thereto in a nitrogen atmosphere, the temperature of the reaction mixture was increased to 35° C., and the reaction mixture was then stirred for 30 minutes under heating. Subsequently, the temperature of the reaction mixture was increased to 85° C., and the reaction mixture was then stirred for 40 hours under heating. After being cooled to room temperature, the reaction mixture was added to 250 mL of water. The produced solid matter was collected by filtration, and washed with 100 mL of acetone. The solid matter was dissolved in 500 mL of cyclohexane heated at 50° C. Subsequently, 2 g of silica gel and 2 g of a metal scavenger were added to the resulting solution to prepare a slurry. The slurry was stirred at 50° C. for one hour, and the silica gel and the metal scavenger were then removed by filtration. Recrystallization from the filtrate was performed. As a result, 178 mg of a white crystal of BTBT derivative b represented by (Chem. 16) was obtained (yield 74%).

$^1$HNMR (300 KHz, CDCl$_3$): δ 8.08 (d, 1H, J=1.8 Hz, H-6), 7.83 (d, 1H, J=8.2 Hz, H-9), 7.78 (d, 1H, J=7.8 Hz, H-4), 7.72 (S, 1H, H-1), 7.61-7.55 (m, 3H, H-8, H-2', -6' of Ph), 7.38-7.35 (m, 3H, H-3', -4', 5' of Ph), 7.29 (dd, 1H, J=7.8 Hz, H-3), 3.77 (t, 2H, J=7 Hz, BTBT-CH$_2$), 1.70 (quint. 2H, J=7 Hz, BTBT-CH$_2$CH$_2$), 1.55-1.27 (m, 14H, CH$_2$×7), 0.88 (t, 3H, J=7 Hz, CH$_3$).

FD-MS: [M]$^+$=480.3

[Chem. 16]

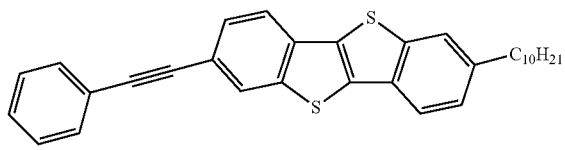

Example 3

The same operation, as that in Example 2 was conducted except that 0.55 g (5.4 mmol) of ethynylbenzene in Example 2 was changed to 0.82 g (5.4 mmol) of 2-ethynylnaphthalene. As a result, 197 mg of a white crystal of BTBT derivative c represented by (Chem. 17) was obtained (yield 74%).

$^1$HNMR (300 MHz, CDCl$_3$): δ 8.48 (d, 1H, H of NaPh), 8.18 (d, 1H, J=1.8 Hz, H-6), 7.88-7.76 (m, 5H, H-9, H-4, 3H of NaPh), 7.72 (m, 3H, H-1, H-8, 3H of NaPh), 7.29 (dd, 1H, J=7.8 Hz, H-3), 2.77 (t, 2H, J=7 Hz, BTBT-CH$_2$), 1.70 (quint. 2H, J=7 Hz, BTBT-CH$_2$CH$_2$), 1.55-1.27 (m, 14H, CH$_2$×7), 0.88 (t, 3H, J=7 Hz, CH$_3$).

FD-MS: [M]$^+$=530.2

[Chem. 17]

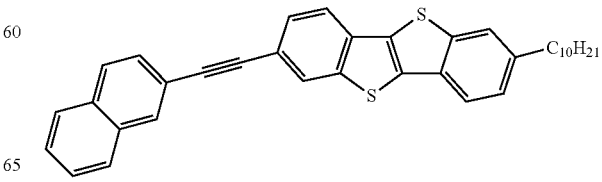

Example 4

The same operation as that in Example 2 was conducted except that 0.55 g (5.4 mmol) of ethynylbenzene in Example 2 was changed to 0.93 g (5.4 mmol) of 1-ethynyl-4-phenylbenzene. As a result, 189 mg of a white crystal of BTBT derivative d represented by (Chem. 18) was obtained (yield 71%).

$^1$HNMR (300 KHz, CDCl$_3$): δ 8.10 (d, 1H, H-6), 7.83 (d, 1H, J=8.2 Hz, H-9), 7.78 (d, 1H, J=7.8 Hz, H-4), 7.72 (s, 1H, H-1), 7.65-7.59 (m, 7H, H-8, 6H of BiPh), 7.45 (t, 2H of BiPh), 7.36 (t, 1H of BiPh), 7.29 (dd, 1H, J=7.8 Hz, H-3), 2.77 (t, 2H, J=7 Hz, BTBT-CH$_2$), 1.70 (quint. 2H, J=7 Hz, BTBT-CH$_2$CH$_2$), 1.55-1.27 (m, 14H, CH$_2$×7), 0.88 (t, 3H, J=7 Hz, CH$_3$).

FD-MS: [M]$^+$=556.2

[Chem. 18]

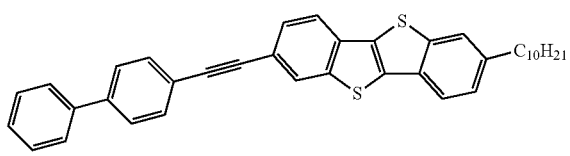

Example 5

The same operation as that in Example 2 was conducted except that 0.55 g (5.4 mmol) of ethynylbenzene in Example 2 was changed to 0.58 g (5.4 mmol) of 3-ethynylthiophene. As a result, 147 mg of a white crystal of BTBT derivative e represented by (Chem. 19) was obtained (yield 60%).

$^1$HNMR (300 MHz, CDCl$_3$)

δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.56 (dd, 1H, H-8), 7.54 (d, 1H of Th), 7.32-7.20 (m, 3H, H-3, 2H of Ph), 2.77 (t, 2H, J=7 Hz, BTBT-CH$_2$), 1.70 (quint. 2H, J=7 Hz, BTBT-CH$_2$CH$_2$), 1.55-1.27 (m, 14H, CH$_2$×7), 0.88 (t, 3H, J=7 Hz, CH$_3$).

FD-MS: [M]$^+$486.2

[Chem. 19]

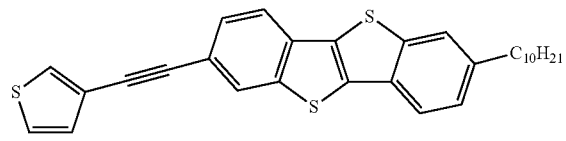

Example 6

The same operation as that in Example 2 was conducted except that 0.55 g (5.4 mmol) of ethynylbenzene in Example 2 was changed to 1.05 g (5.4 mmol) of 1-ethynyl-4-phenoxybenzene. As a result, 62 mg of a white crystal of BTBT derivative f represented by (Chem. 20) was obtained (yield 22%).

$^1$HNMR (300 MHz, CDCl$_3$):

δ 8.07 (d, 1H, J=1.8 Hz, H-6), 7.80 (d, 1H, J=8.2 Hz, H-9), 7.78 (d, 1H, J=7.8 Hz, H-4), 7.72 (s, 1H, H-1), 7.54 (dd, 1H, J=8.2 Hz, H-8), 7.51 (d, 2H of Ph), 7.36 (m, 2H of Ph), 7.29 (dd, 1H, J=7.8 Hz, H-3), 7.15 (tt, 1H of Ph), 7.06 (dd, 2H of Ph), 6.98 (dd, 2H of Ph), 2.77 (t, 2H, J=7 Hz, BTBT-CH$_2$), 2.37 (s, 3H, Ph-CH$_3$), 1.70 (quint. 2H, J=7 Hz, BTBT-CH$_2$CH$_2$), 1.55-1.27 (m, 14H, CH$_2$×7), 0.88 (h, 3H, J=7 Hz, CH$_3$).

FD-MS: [M]$^+$=572.2

[Chem. 20]

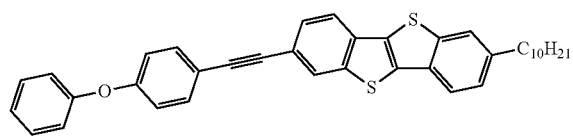

Example 7

The same operation as that in Example 2 was conducted except that 0.55 g (5.4 mmol) of ethynylbenzene in Example 2 was changed to 0,63 g (5.4 mmol) of 4-ethynyltoluene. As a result, 94 mg of a white crystal of BTBT derivative g represented by (Chem. 21) was obtained (yield 38%).

$^1$HNMR (300 MHz, CDCl$_3$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.57 (dd, 1H, J=8.2 Hz, H-3), 7.44 (d, 2H, H-2', -6' of Ph), 7.29 (dd, 1H, J=7.8 Hz, H-3), 7.16 (d, 2H, H-3', -5' of Ph), 2.77 (t, 2H, J=7 Hz, BTBT-CH$_2$), 2.37 (s, 3H, Ph-CH$_3$), 1.70 (quint. 2H, J=7 Hz, BTBT-CH$_2$CH$_2$), 1.55-1.27 (m, 14H, CH$_2$×7), 0.88 (t, 3H, J=7 Hz, CH$_3$).

FD-MS: [M]$^+$=494.3

[Chem. 21]

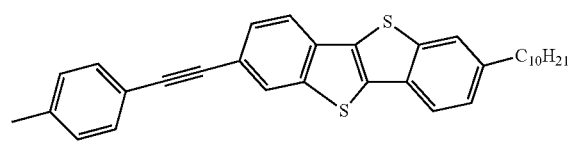

Example 8

The same operation, as that in Example 2 was conducted except that 0.55 g (5.4 mmol) of ethynylbenzene in Example 2 was changed to 0.78 g (5.4 mmol) of 1-ethynyl-4-propyl benzene. As a result, 102 mg of a white crystal of BTBT derivative h represented by (Chem. 22) was obtained (yield 39%).

$^1$HNMR (300 MHz, CDCl$_3$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.57 (dd, 1H, J=8.2 Hz, H-8), 7.44 (d, 2H, H-2', -6' of Ph), 7.29 (dd, 1H, J=7.8 Hz, H-3), 7.16 (d, 2H, H-3', -5' of Ph), 2.77 (t, 2H, J=7 Hz, BTBT-CH$_2$), 2.63 (t, 2H, J=7 Hz, Ph-CH$_2$), 1.63 (quint. 2H, J=7 Hz, BTBT-CH$_2$CH$_2$), 1.55-1.27 (m, 16H, CH$_2$×8), 0.96 (t, 3H, J=7 Hz, CH$_3$), 0.88 (t, 3H, J=7 Hz, CH$_3$).

FD-MS: [M]$^+$=523.3

[Chem. 22]

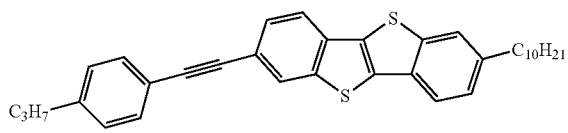

Example 9

The same operation as that in Example 2 was conducted except that 0.65 g (5.4 mmol 1 of ethynylbenzene in Example 2 was changed to g (5.4 mmol) of 1-ethynyl-4-t-butylbenzene. As a result, 113 mg of a white crystal of BTBT derivative i represented by (Chem. 23) was obtained (yield 40%).

$^1$HNMR (300 MHz, CDCl$_3$):
δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.57 (dd, 1H, J=8.2 Hz, H-8), 7.50 (d, 2H, H-2', -6' of Ph), 7.39 (d, 2H, H-3', -5' of Ph), 7.29 (dd, 1H, J=7.8 Hz, H-3), 2.7 (t, 2H, J=7 Hz, BTBT-CH$_2$), 1.63 (quint. 2H, J=7 Hz, BTBT-CH$_2$CH$_2$), 1.55-1.27 (m, 23H, CH$_2$×7, CH$_3$×3), 0.88 (t, 3H, J=7 Hz, CH$_3$).
FD-MS: [M]$^+$536.26

[Chem. 23]

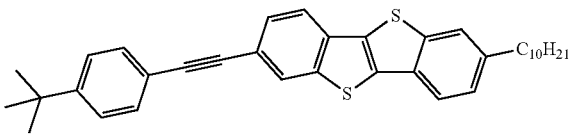

Example 10

The same operation as that in Example 2 was conducted except that 0.55 g (5.4 mmol) of ethynylbenzene in Example 2 was changed to 0.93 g (5.4 mmol) of 1-ethynyl-4-pentyl-benzene. As a result, 93 mg of a white crystal of BTBT derivative j represented by (Chem. 24) was obtained (yield 34%).

$^1$HNMR (300 MHz, CDCl$_2$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.57 (dd, 1H, J=8.2 Hz, H-8), 7.44 (d, 2H, H-2', -6' of Ph), 7.29 (dd, 1H, J=7.8 Hz, H-3), 7.16 (d, 2H, H-3', H-5' of Ph), 2.77 (t, 2H, J=7 Hz, BTBT-CH$_2$CH$_2$), 2.63 (t, 2H, Ph-CH$_2$), 1.70 (quint. 2H, J=7 Hz, Ph-CH$_2$CH$_2$), 1.63 (quint. 2H, J=7 Hz, BTBT-CH$_2$CH$_2$), 1.55-1.27 (m, 18H, CH$_2$×9), 0.88 (t, 6H, J=7 Hz, CH$_3$×2).
FD-MS: [M]$^+$550.3

[Chem. 24]

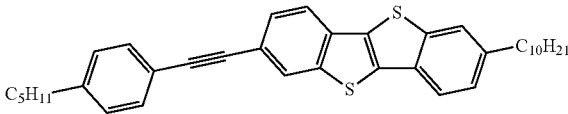

Example 11

The same operation as that in Example 2 was conducted except that 0.55 g (5.4 mmol) of ethynylbenzene in Example 2 was changed to 1.0 g (5.4 mmol) of 1-ethynyl-4-hexyl-benzene. As a result, 107 mg of a white crystal of BTBT derivative k represented by (Chem. 25) was obtained (yield 38%).

$^1$HNMR (300 MHz, CDCl$_3$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.57 (dd, 1H, J=8.2 Hz, H-8), 7.44 (d, 2H, H-2', -6' of Ph), 7.29 (dd, 1H, J=7.8 Hz, H-3), 7.16 (d, 2H, H-3', -5' of Ph), 2.77 (t, 2H, J=7 Hz, BTBT-CH$_2$), 2.63 (t, 2H, Ph-CH$_2$), 1.70 (quint. 2H, J=7 Hz, Ph-CH$_2$CH$_2$), 1.63 (quint. 2H, J=7 Hz, BTBT-CH$_2$CH$_2$), 1.55-1.27 (m, 20H, CH$_2$×10), 0.88 (t, 6H, J=7 Hz, CH$_3$×2).

[Chem. 25]

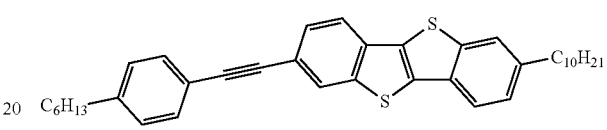

Example 12

The same operation as that in Example 2 was conducted except that 0.55 g (5.4 mmol) of ethynylbenzene in Example 2 was changed to 0.56 g (5.4 mmol) of 3-ethynyl-pyridine. As a result, 44 mg of a white crystal of BTBT derivative 1 represented by (Chem. 26) was obtained (yield 18%).

$^1$HNMR (300 MHz, CDCl$_2$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.57 (dd, 1H, J=8.2 Hz, H-8), 7.44 (d, 2H, H-2', -6' of Ph), 7.29 (dd, 1H, J=7.8 Hz, H-3), 7.16 (d, 2H, K-3', -5' of Ph), 2.7 (t, 2H, J=7 Hz, BTBT-CH$_2$), 2.63 (t, 2H, Ph-CH$_2$), 1.70 (quint. 2H, J=7 Hz, Ph-CH$_2$CH$_2$), 1.63 (quint. 2H, J=7 Hz, BTBT-CH$_2$CH$_2$), 1.55-1.27 (m, 20H, CH$_2$×10), 0.88 (t, 6H, J=7 Hz, CH$_3$×2).

[Chem. 26]

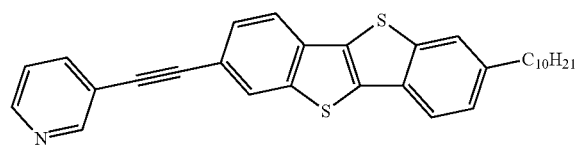

Example 13

First, BTBT (6 g, 25 mmol) was added to 300 mL of dichloromethane, and the mixture was stirred in a nitrogen gas atmosphere until the temperature became −10° C. Next, aluminum chloride (13.3 g, 0.1 mol) was added to the mixture, and the temperature was decreased to −70° C. After the temperature reached −70° C., tetradecanoyl chloride (6.9 g, 25 mmol) was added dropwise over a period of 20 minutes, and the resulting reaction mixture was stirred for 3.5 hours. The reaction mixture was added, to 600 g of water, and 200 g of dichloromethane was then added thereto. The mixture was transferred to a separatory funnel. The resulting liquid was separated, and the lower layer was washed with 300 g of water. This operation was conducted twice, and an organic layer was then concentrated. The resulting precipitate was dissolved in 300 g of toluene under heating, and then recrystallized at room temperature. As a result, 9.7 g of a yellow crystal of 2-(tetradecyl-1-one)-BTBT was obtained (yield 36%).

Subsequently, 2-(tetradecyl-1-one)-BTBT (9.0 g, 20 mmol), 85.5% potassium hydroxide (3.5 g, 53 mmol), and hydrazine monohydrate (6.5 g, 124 mmol) were added to 300 mL of diethylene glycol. The reaction mixture was stirred in a nitrogen atmosphere, the temperature was increased to 100° C., and stirring was performed for one hour. Subsequently, the temperature was increased to 10° C., water was removed from the reaction system using a decanter, and the reaction mixture was stirred under heating for 4 hours. The reaction mixture was cooled to room temperature. A solid matter precipitated in the reaction mixture was then collected by filtration, and washed with water and ethanol in that order. The solid matter after the washing was vacuum-dried at 70° C. to obtain 8.5 g of 2-tetradecyl-BTBT (yield 97%)

Furthermore, 2-tetradecyl-BTBT (8.5 g, 19.5 mmol) was added to 150 mL of chloroform and 150 mL of acetic acid. The mixture was stirred at room temperature in a nitrogen gas atmosphere, and 3.9 g (24.4 mmol) of bromine was added dropwise over a period of 20 minutes. Subsequently, stirring was performed for 10 hours and the reaction was terminated. Subsequently, 200 mL of water was added to the reaction mixture. The reaction mixture was separated, and the lower layer was collected. The lower layer was concentrated and dried to obtain a crude solid. The solid was recrystallized from acetone to obtain 5.82 g of a white crystal of 2-tetradecyl-7-bromo BTBT (yield 58%).

Lastly, copper iodide (0.11 g, 0.0 mmol), bis(triphenylphosphine)palladium(II) dichloride (0.08 g, 0.1 mmol), and 36 mL of triethylamine were added to 2-tetradecyl-7-bromo BTBT (258 mg, 0.5 mmol), and nitrogen gas was bubbled at room temperature for 15 minutes. Next, 0.55 g (5.4 mmol) of ethynylbenzene was added, thereto in a nitrogen atmosphere, the temperature of the reaction mixture was increased to 35° C., and the reaction mixture was then stirred for 30 minutes under heating. Subsequently, the temperature of the reaction mixture was increased to 85° C., and the reaction mixture was then stirred for 40 hours under heating. After being cooled, to room temperature, the reaction mixture was added to 250 mL of water. The produced solid matter was collected by filtration, and washed with 100 mL of acetone. The solid matter was dissolved in 500 mL of cyclohexane heated at 50° C. Subsequently, 2 g of silica gel and 2 g of a metal scavenger were added to the resulting solution to prepare a slurry. The slurry was stirred at 50° C. for one hour, and the silica gel and the metal scavenger were then removed by filtration. Recrystallization from the filtrate was performed. As a result, 180 mg of a white crystal of BTBT derivative m represented by (Chem. 27) was obtained (yield 67%).

$^1$HNMR (300 MHz, CDCl$_3$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.61-7.55 (m, 3H, H-8, H-2', -6' of Ph), 7.38-7.35 (m, 3H, H-3', -4', -5' of Ph), 7.29 (dd, 1H, J=7.8 Hz, H-3), 2.77 (t, 2H, J=7 Hz, BTBT-CH$_2$), 1.70 (quint. 2H, J=7 Hz, BTBT-CH$_2$CH$_2$), 1.55-1.27 (m, 22H, CH$_2$×11), 0.88 (t, 3H, J=7 Hz, CH$_3$).

FD-MS: [M]$^+$=536.3

[Chem. 27]

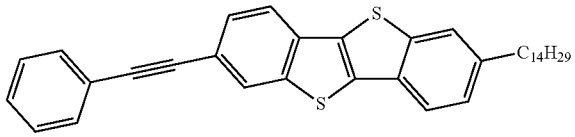

Example 14

The same operation as that in Example 13 was conducted except that 0.55 g (5.4 mmol) of ethynylbenzene in Example 13 was changed to 0.63 g (5.4 mmol) of 4-ethynyltoluene. As a result, 124 mg of a white crystal of BTBT derivative n represented by (Chem. 28) was obtained (yield 45%).

$^1$HNMR (300 MHz, CDCl$_3$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.57 (dd, 1H, J=8.2 Hz, H-8), 7.44 (d, 2H, H-2', -6' of Ph), 7.29 (dd, 1H, J=7.8 Hz, H-3), 7.16 (d, 2H, H-3', -5' of Ph), 2.77 (t, 2H, J=7 Hz, BTBT-CH$_2$), 2.37 (s, 3H, Ph-CH$_3$), 1.70 (quint. 2H, J=7 Hz, BTBT-CH$_2$CH$_2$), 1.55-1.27 (m, 22H, CH$_2$×11), 0.88 (t, 3H, J=7 Hz, CH$_3$).

FD-MS: [M]$^+$=550.3

[Chem. 28]

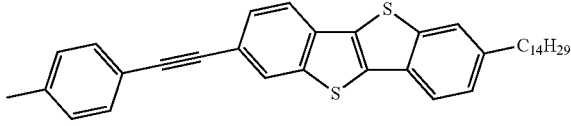

Example 15

The same operation as that in Example 13 was conducted except that 0.55 g (5.4 mmol) of ethynylbenzene in Example 13 was changed to 0.93 g (5.4 mmol) of 1-ethynyl-4-pentylbenzene. As a result, 162 mg of a white crystal of BTBT derivative o represented by (Chem. 29) was obtained (yield 53%).

$^1$HNMR (300 MHz, CDCl$_3$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.57 (dd, 1H, J=8.2 Hz, H-8), 7.44 (d, 2H, H-2', -6' of Ph), 7.29 (dd, 1H, J=7.8 Hz, H-3), 7.16 (d, 2H, H-3', -5' of Ph), 2.77 (t, 2H, J=7 Hz, BTBT-CH$_2$), 2.63 (t, 2H, Ph-CH$_2$), 1.70 (quint. 2H, J=7 Hz, Ph-CH$_2$CH$_2$), 1.63 (quint. 2H, J=7 Hz, BTBT-CH$_2$CH$_2$), 1.55-1.27 (m, 26H, CH$_2$×13), 0.88 (t, 6H, J=7 Hz, CH$_2$×2).

FD-MS: [M]$^+$=606.3

[Chem. 29]

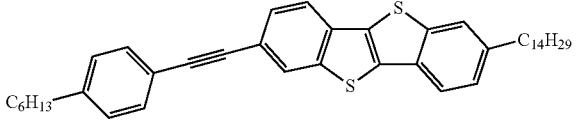

Example 16

First, BTBT (6 g, 25 mmol) was added to 300 mL of dichloromethane, and the mixture was stirred in a nitrogen gas atmosphere until, the temperature became −10° C. Next, aluminum chloride (13.3 g, 0.1 mol) was added to the mixture, and the temperature was decreased to −70° C. After the temperature reached −70° C., octanoyl chloride (3.8 g, 25 mmol) was added dropwise over a period of 20 minutes, and the resulting reaction mixture was stirred for 3.5 hours. The reaction mixture was added to 600 g of water, and 200 g of dichloromethane was then added thereto. The mixture was transferred to a separatory funnel. The resulting liquid was separated, and the lower layer was washed with 300 g of water. This operation was conducted twice, and an organic layer was then concentrated. The resulting precipitate was dissolved in 250 g of toluene under heating, and then recrystallized at room temperature. As a result, 7.9 g of a yellow crystal of 2-(octyl-1-one)-BTBT was obtained (yield 84%).

Subsequently, 2-(octyl-1-one)-BTBT (7.3 g, 20 mmol), 85.5% potassium hydroxide (3.5 g, 53 mmol), and hydrazine monohydrate (6.5 g, 124 mmol) were added to 300 mL of diethylene glycol. The resulting mixture was stirred in a nitrogen atmosphere, the temperature was increased to 10° C., and stirring was performed for one hour. Subsequently, the temperature was increased to 170° C., water was removed from the reaction system using a decanter, and the reaction mixture was stirred under heating for 4 hours. The reaction mixture was cooled to room temperature. A solid matter precipitated in the reaction mixture was then collected by filtration, and washed with water and ethanol in that order. The solid matter after the washing was vacuum-dried at 70° C. to obtain 6.6 g of 2-octyl-BTBT (yield 94%). Furthermore, 2-octyl-BTBT (6.5 g, 18.5 mmol) was dissolved in 200 mL of chloroform. The resulting solution was then cooled to 0° C., and 3.7 g (23.1 mmol) of bromine was added dropwise to the solution over a period of 20 minutes. Furthermore, stirring was conducted at 0° C. for 0.5 hours, and the temperature was then increased to room temperature. Stirring was conducted for three hours, and the reaction was terminated. Water was added to the solution, and the resulting mixture was separated. The lower layer was collected, and concentrated and dried to obtain a crude solid. The solid was recrystallized from acetone to obtain 4.39 g of a white crystal of 2-octyl-7-bromo BTBT (yield 55%).

Lastly, copper iodide (0.11 g, 0.6 mmol), bis(triphenylphosphine)palladium(II) dichloride (0.08 g, 0.1 mmol), and 36 mL of triethylamine were added to 2-octyl-7-bromo BTBT (216 mg, 0.5 mmol), and nitrogen gas was bubbled at room temperature for 15 minutes. Next, 0.93 g (5.4 mmol) of 1-ethynyl-4-pentylbenzene was added thereto in a nitrogen atmosphere, the temperature of the reaction mixture was increased to 35° C., and the reaction mixture was then stirred for 30 minutes under heating. Subsequently, the temperature of the reaction mixture was increased to 85° C., and the reaction mixture was then stirred for 40 hours under heating. After being cooled to room temperature, the reaction mixture was added to 250 mL of water. The produced solid matter was collected by filtration, and washed with 100 mL of acetone. The solid matter was dissolved in 500 ml, of cyclohexane heated at 50° C. Subsequently, 2 g of silica gel and 2 g of a metal scavenger were added to the resulting solution to prepare a slurry. The slurry was stirred at 50° C. for one hour, and the silica gel and the metal scavenger were then removed by filtration. Recrystallization from, the filtrate was performed. As a result, 118 mg of a white crystal of BTBT derivative p represented by (Chem. 30) was obtained (yield 45%).

¹HNMR (300 MHz, CDCl₃): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.57 (dd, 1H, J=8.2 Hz, H-8), 7.44 (d, 2H, H-2', -6' of Ph), 7.29 (dd, 1H, J=7.8 Hz, H-3), 7.16 (d, 2H, H-3', -5' of Ph), 2.77 (t, 2H, J=7 Hz, BTBT-CH₂), 2.63 (t, 2H, Ph-CH₂), 1.70 (quint. 2H, J=7 Hz, Ph-CH₂CH₂), 1.63 (quint. 2H, J=7 Hz, BTBT-CH₂CH₂), 1.55-1.27 (m, 14H, CH₂×7), 0.88 (t, 6H, J=7 Hz, CH₂×2).

FD-MS: [M]⁺522.2

[Chem. 30]

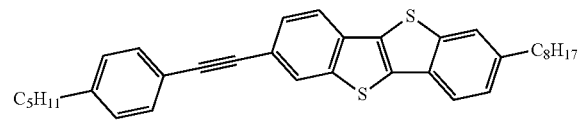

Example 17

First, BTBT (6 g, 25 mmol) was added to 300 ml, of dichloromethane, and the mixture was stirred in a nitrogen gas atmosphere until the temperature became −10° C. Next, aluminum chloride (13.3 g, 0.1 mol) was added to the mixture, and the temperature was decreased to −70° C. After the temperature reached −70° C., hexanoyl chloride (3.37 g, 25 mmol) was added dropwise over a period of 30 minutes, and the resulting reaction mixture was stirred for 3.5 hours. The reaction mixture was added to 600 g of water, and 200 g of dichloromethane was then added thereto. The mixture was transferred to a separatory funnel. The resulting liquid was separated, and the lower layer was washed with 300 g of water. This operation was conducted twice, and an organic layer was then concentrated. The resulting precipitate was dissolved in 250 g of toluene under heating, and then recrystallized at room temperature. As a result, 7.4 g of a yellow crystal of 2-(hexyl-1-one)-BTBT was obtained (yield 88%).

Subsequently, 3-(hexyl-1-one)-BTBT (6.8 g, 20 mmol), 85.5% potassium hydroxide (3.5 g, 53 mmol), and hydrazine monohydrate (6.5 g, 124 mmol) were added to 300 mL of diethylene glycol. The resulting mixture was stirred in a nitrogen atmosphere, the temperature was increased to 100° C., and stirring was performed for one hour. Subsequently, the temperature was increased to 170° C., water was removed from the reaction system using a decanter, and the reaction mixture was stirred under heating for 4 hours. The reaction mixture was cooled to room temperature. A solid matter precipitated in the reaction mixture was then collected by filtration, and washed with water and ethanol in that order. The solid matter after the washing was vacuum-dried at 70° C. to obtain 6.0 g of 2-hexyl-BTBT (yield 92%). Furthermore, 2-hexyl-BTBT (6.0 g, 18.5 mmol) was dissolved in 200 mL of chloroform. The resulting solution was then cooled to 0° C., and 3.7 g (23.1 mmol) of bromine was added dropwise to the solution over a period of 20 minutes. Furthermore, stirring was conducted at 0° C. for 0.5 hours, and the temperature was then increased to room temperature. Stirring was conducted for three hours, and the reaction was terminated. Water was added to the solution, and the resulting mixture was separated. The lower layer was collected, and concentrated and dried to obtain a crude solid. The solid was recrystallized from acetone to obtain 4.3 g of a white crystal of 2-hexyl-7-bromo BTBT (yield 58%).

Lastly, copper iodide (0.11 g, 0.6 mmol), bis(triphenylphosphine)palladium(II) dichloride (0.08 g, 0.1 mmol), and 36 mL of triethylamine were added to 2-hexyl-bromo BTBT (202 mg, 0.5 mmol), and nitrogen gas was bubbled at room temperature for 15 minutes. Next, 0.55 g (5.4 mmol) of ethynylbenzene was added thereto in a nitrogen atmosphere, the temperature of the react ion mixture was increased to 35° C., and the reaction mixture was then stirred for 30 minutes under heating. Subsequently, the temperature of the reaction mixture was increased to 85° C., and the reaction mixture was then stirred for 40 hours under heating. After being cooled to room temperature, the reaction mixture was added to 250 mL of water. The produced solid matter was collected by filtration, and washed with 100 mL of acetone. The solid matter was dissolved in 500 mL of cyclohexane heated at 50° C. Subsequently, 2 g of silica gel and 2 g of a metal scavenger were added to the resulting solution to prepare a slurry. The slurry was stirred at 50° C. for one hour, and the silica gel and the metal scavenger were then removed by filtration. Recrystallization from the filtrate was performed. As a result, 175 mg of a white crystal of BTBT derivative q represented by (Chem. 31) was obtained (yield 83%).

$^1$HNMR (300 MHz, CDCl$_3$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.61-7.55 (m, 3H, H-8, H-2', -6' of Ph), 7.38-7.35 (m, 3H, H-3', -4', -5' of Ph), 7.29 (dd, 1H, J=7.8 Hz, H-3), 2.77 (t, 2H, J=7 Hz, BTBT-CH$_2$), 1.70 (quint. 2H, J=7 Hz, BTBT-CH$_2$CH$_2$), 1.55-1.27 (m, 6H, CH$_3$×3), 0.88 (t, 3H, J=7 Hz, CH$_3$).

FD-MS: [M]$^+$424.1

[Chem. 31]

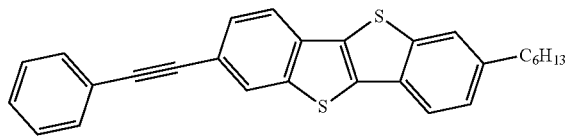

Example 18

The same operation as that in Example 17 was conducted except that 0.55 g (5.4 mmol) of ethynylbenzene in Example 1 was changed to 0.63 g (5.4 mmol) of 4-ethynyltoluene. As a result, 107 mg of a white crystal of BTBT derivative r represented by (Chem. 32) was obtained (yield 49%).

$^1$HNMR (300 KHz, CDCl$_3$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.57 (dd, 1H, J=8.2 Hz, H-8), 7.44 (d, 2H, H-2', -6' of Ph), 7.29 (dd, 1H, J=7.8 Hz, H-3), 7.16 (d, 2H, H-3', -5' of Ph), 2.77 (t, 2H, J=7 Hz, BTBT-CH$_2$), 2.37 (s, 3H, Ph-CH$_3$), 1.70 (quint. 2H, J=7 Hz, BTBT-CH$_2$CH$_2$), 1.55-1.27 (m, 6H, CH$_2$×3), 0.88 (t, 3H, J=7 Hz, CH$_3$).

FD-MS: [M]$^+$=438.2

[Chem. 32]

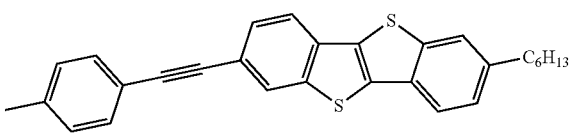

Example 19

The same operation as that in Example 17 was conducted except that 0.55 g (5.4 mmol) of ethynylbenzene in Example 17 was changed to 0.93 g (5.4 mmol) of 1-ethynyl-4-pentylbenzene. As a result, 114 mg of a white crystal of BTBT derivative s represented by (Chem. 33) was obtained (yield 46%).

$^1$HNMR (300 KHz, CDCl$_3$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.5 (dd, 1H, J=8.2 Hz, H-8), 7.44 (d, 2H, H-2', -6' of Ph), 7.29 (dd, 1H, J=7.8 Hz, H-3), 7.16 (d, 2H, H-3', -5' of Ph), 2.7 (t, 2H, J=7 Hz, BTBT-CH$_2$), 2.63 (t, 2H, Ph-CH$_2$), 1.70 (quint. 2H, J=7 Hz, Ph-CH$_2$CH$_2$), 1.63 (quint. 2H, J=7 Hz, BTBT-CH$_2$CH$_2$), 1.55-1.27 (m, 10H, CH$_2$×5), 0.88 (t, 6H, J=7 Hz, CH$_3$×2).

FD-MS: [M]$^+$=494.2

[Chem. 33]

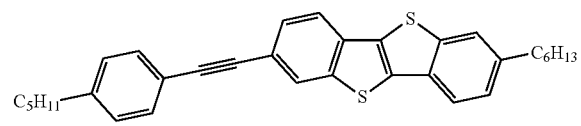

Example 20

The same operation as that in Example 17 was conducted, except that 0.55 g (5.4 mmol) of ethynylbenzene in Example 17 was changed to 0.58 g (5.4 mmol) of 3-ethynylthiophene. As a result, 1.66 mg of a white crystal of BTBT derivative t represented, by (Chem. 34) was obtained (yield 77%).

$^1$HNMR: (300 MHz, CDCl$_3$): δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.56 (dd, 1H, H-8), 7.54 (d, 1H of Th), 7.32-7.20 (m, 3H, H-3, 2H of Th), 2.77 (t, 2H, J=7 Hz, BTBT-CH$_2$), 1.70 (quint. 2H, J=7 Hz, BTBT-CH$_3$CH$_3$), 1.55-1.27 (m, 6H, CH$_2$×3), 0.88 (t, 3H, J=7 Hz, CH$_3$).

FD-MS: [M]$^+$=430.1

[Chem. 34]

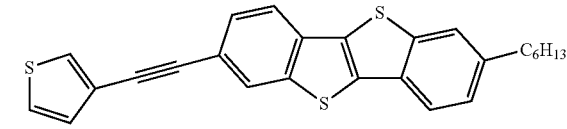

Example 21

First, BTBT (6 g, 25 mmol) was added to 300 mL of dichloromethane, and the mixture was stirred in a nitrogen gas atmosphere until the temperature became –10° C. Next, aluminum chloride (13.3 g, 0.1 mol) was added to the mixture, and the temperature was decreased to –70° C. After the temperature reached –0° C., 10-bromodecanoyl chloride (6.73 g, 25 mmol) was added dropwise over a period of 20 minutes, and the resulting reaction mixture was stirred for 3.5 hours. The reaction mixture was added to 600 g of water, and 200 g of dichloromethane was then added thereto. The mixture was transferred to a separator/funnel. The resulting liquid was separated, and the lower layer was washed with 300 g of water. This operation was conducted twice, and an organic layer was then concentrated. The resulting precipitate was dissolved in 250 g of toluene under heating, and then recrystallized at room temperature. As a result, 9.0 g of a yellow crystal of 2-(10-bromodecyl-1-one)-BTBT was obtained (yield 76%).

Subsequently, 2-(10-bromodecyl-1-one)-BTBT (8.5 g, 18 mmol), 85.5% potassium hydroxide (3.2 g, 48 mmol), and hydrazine monohydrate (5.85 g, 112 mmol) were added to 300 mL of diethylene glycol. The resulting mixture was stirred in a nitrogen atmosphere, the temperature was increased to 100° C., and stirring was performed for one hour. Subsequently, the temperature was increased to 170° C., water was removed from the reaction system using a decanter, and the reaction mixture was stirred under heating for 4 hours. The reaction mixture was cooled to room temperature. A solid matter precipitated in the reaction mixture was then collected by filtration, and washed with water and ethanol in that order. The solid matter after the washing was vacuum-dried at 70° C. to obtain 7.0 g of 2-(10-bromodecyl)-BTBT (yield 85%). Furthermore, 2-(10-bromodecyl)-BTBT (6.9 g, 15 mmol) was dissolved in 200 mL of chloroform. The resulting solution was then cooled to 0° C., and 3.0 g (18.7 mmol) of bromine was added dropwise to the solution over a period of 20 minutes. Furthermore, stirring was conducted at 0° C. for 0.5 hours, and the temperature was then increased to room temperature. Stirring was conducted for three hours, and the reaction was terminated. Water was added to the solution, and the resulting mixture was separated. The lower layer was collected, and concentrated and dried to obtain a crude solid. The solid was recrystallized from acetone to obtain 3.63 g of a white crystal of 2-(10-bromodecyl)-7-bromo BTBT (yield 48%).

Next, copper iodide (0.88 g, 4.8 mmol), bis(triphenylphosphine)palladium(II) dichloride (0.64 g, 0.8 mmol), and 280 mL of triethylamine were added to 2-(10-bromodecyl)-7-bromo BTBT (2.16 g, 4 mmol), and nitrogen gas was bubbled at room temperature for 15 minutes. Next, 4.4 g (43 mmol) of ethynylbenzene was added thereto in a nitrogen atmosphere, the temperature of the reaction mixture was increased to 35° C., and the reaction mixture was then stirred for 30 minutes under heating. Subsequently, the temperature of the reaction mixture was increased to 85° C., and the reaction mixture was then stirred for 40 hours under heating. After being cooled to room temperature, the reaction mixture was added to 1 L of water. The produced solid matter was collected by filtration, and washed with 300 mL of acetone. The solid matter was dissolved in 800 mL of cyclohexane heated at 50° C. Subsequently, 15 g of silica gel and 15 g of a metal scavenger were added to the resulting solution to prepare a slurry. The slurry was stirred at 50° C. for one hour, and the silica gel and the metal scavenger were then removed by filtration. Recrystallization from the filtrate was performed. As a result, 1.45 g of a white crystal of 2-(10-bromodecyl)-7-phenylethynyl BTBT was obtained (yield 65%).

Lastly, 15 mL of THF, 15 mL of dimethylformamide (DMF), ethyl mercaptan (198 mg, 3.2 mmol), cesium carbonate (1.04 g, 3.2 mmol), and tetrabutylammonium iodo (1.18 g, 3.2 mmol) were stirred at 0° C. A solution prepared by dissolving 2-(10-bromodecyl)-7-phenylethynyl BTBT (447 mg, 0.8 mmol) in 10 mL of THF was added dropwise thereto. The reaction mixture was stirred at the same temperature for 24 hours, and 1.5 mL of a saturated ammonium chloride solution was added thereto to terminate the reaction. The reaction mixture was concentrated, and then poured into 100 mL of water. The precipitated crystal was collected by filtration. The crystal was purified by silica gel chromatography (cyclohexane/chloroform=85/15) to obtain 133 mg of a white crystal of BTBT derivative u represented by (Chem. 35) (yield 26%).

$^1$HNMR (300 MHz, CDCl$_3$):

δ 8.08 (d, 1H, J=1.8 Hz, H-6), 7.83 (d, 1H, J=8.2 Hz, H-9), 7.78 (d, 1H, J=7.8 Hz, H-4), 7.72 (s, 1H, H-1), 7.61-7.55 (m, 3H, H-8, H-2', -6' of Ph), 7.38-7.35 (m, 3H, H-3', -4', -5' of Ph), 7.29 (dd, 1H, J=7.8 Hz, H-3), 2.77 (t, 2H, J=7 Hz, BTBT-CH$_2$), 2.49-2.56 (4H, —CH$_2$—S—CH$_2$—), 1.70 (q, 2H, BTBT-CH$_2$CH$_2$), 1.30-1.60 (m, 14H, —CH$_2$—), 1.25 (t, 3H, CH$_3$).

FD-MS: [M]$^+$=540.2

[Chem. 35]

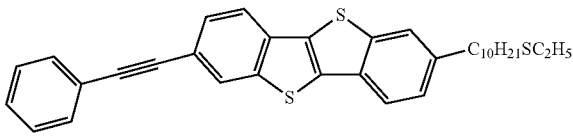

Example 22

Molecular sieves 4 A (0.5 g) and cesium hydroxide monohydrate (274 mg, 1.6 mmol) were added while stirring 2-(10-bromodecyl)-7-phenylethynyl BTBT (4.47 mg, 0.8 mmol) obtained in Example 21, 10 mL of amyl alcohol, 20 mL of dehydrated THF, and 12 mL of dehydrated DMF at room temperature in a nitrogen atmosphere. The resulting reaction mixture was further stirred for 24 hours. Furthermore, 100 mL of chloroform was added to the reaction mixture, and the mixture was filtered. The filtrate was washed with water and a saturated saline solution in that order, and an organic layer was concentrated. The residue was purified by silica gel chromatography (cyclohexane/chloroform=3/1) to obtain 56 mg of a white crystal of BTBT derivative v represented by (Chem. 36) (yield 12%).

$^1$HNMR (300 MHz, CDCl$_3$):

δ 8.08 (d, 1H, J=1.8 Hs, H-6), 7.83 (d, 1H, J=8.2 Hz, H-9), 7.78 (d, 1H, J=7.8 Hz, H-4), 7.72 (s, 1H, H-1), 7.61-7.55 (m, 3H, H-8, H-2', -6' of Ph), 7.38-7.35 (m, 3H, H-3', -4', -5' of Ph), 7.29 (dd, 1H, J=7.8 Hz, H-3), 3.37 (t, 4H, —CH$_2$—O—CH$_2$—), 2.77 (t, 2H, J=7 Hz, BTBT-CH$_2$), 1.70 (q, 2H, BTBT-CH$_2$CH$_2$), 1.30-1.60 (m, 20H, —CH$_2$—), 0.90 (t, 3H, CH$_3$).

FD-MS: [M]$^+$560.3

[Chem. 36]

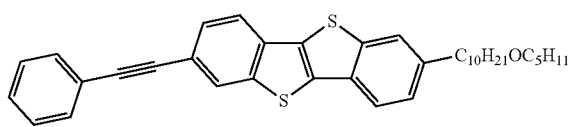

Example 23 to 44

With regard to BTBT derivatives a to v obtained in Examples 1 to 22, the transistor evaluation was performed by the method described above. The results are shown in Table 1. The results of the observation of liquid crystal phases are shown in FIGS. 2 to 23.

Comparative Example 1

A compound represented by (Chem. 37) was synthesized by the method described in International Publication No. WO 2006/077888. With regard to the prepared compound, the observation of a liquid crystal phase was performed as in Examples. According to the result, a liquid crystal phase could not be observed. Evaluation results of a transistor prepared as in Examples are shown in Table 1.

[Chem. 37]

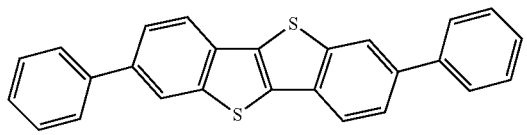

Comparative Example 2

A compound represented by (Chem. 38) was synthesized by the method described in Japanese Unexamined Patent Application Publication No. 2013-1442. With regard to the prepared compound, the observation of a liquid crystal phase was performed as in Examples. According to the result, a high-order liquid crystal phase could not foe observed. Evaluation results of a transistor prepared as in Examples are shown in Table 1.

[Chem. 38]

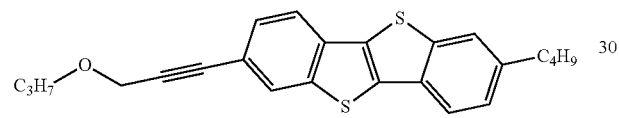

TABLE 1

Figure 2:
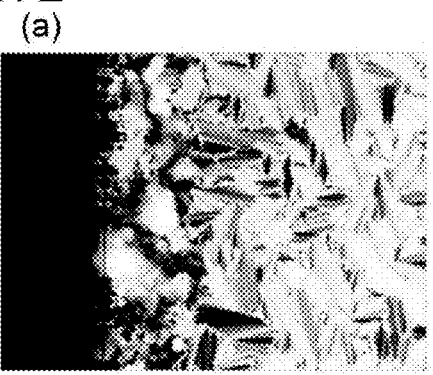
FIG. 2 includes (a) an example of a polarizing microscope photograph (crystal phase) showing a polarizing microscope texture at room temperature of compound a obtained in Example 1, and (b) an example of a polarizing microscope photograph (high-order liquid crystal phase) showing a polarizing microscope texture of a phase in a high-temperature range adjacent to the crystal phase.
Figure 2:
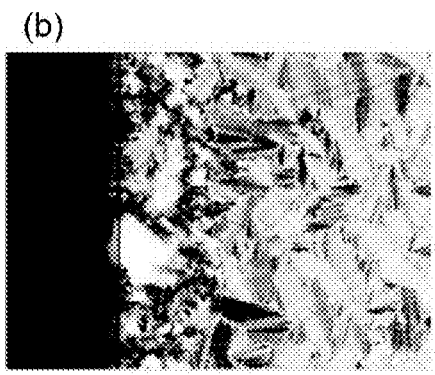
Figure 3:
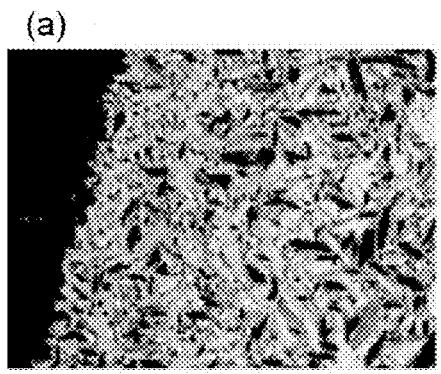
FIG. 3 includes (a) an example of a polarizing microscope photograph (crystal phase) showing a polarizing microscope texture at room temperature of compound b obtained in Example 2, and (b) an example of a polarizing microscope photograph (high-order liquid crystal phase) showing a polarizing microscope texture of a phase in a high-temperature range adjacent to the crystal phase.
Figure 3:
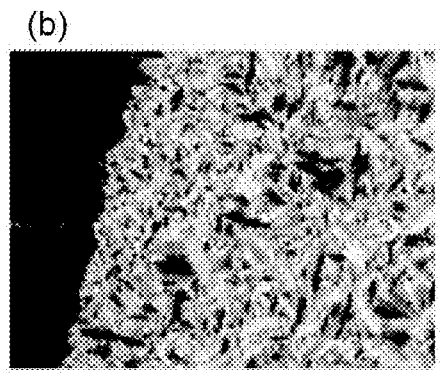
Figure 4:
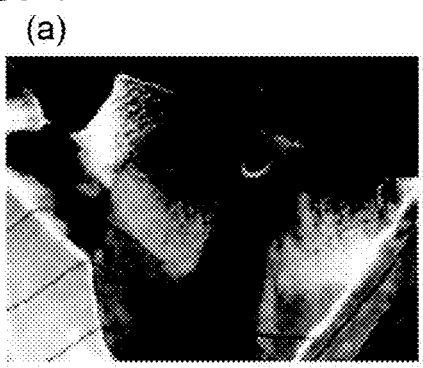
FIG. 4 includes (a) an example of a polarizing microscope photograph (crystal phase) showing a polarizing microscope texture at room temperature of compound c obtained in Example 3, and (b) an example of a polarizing microscope photograph (high-order liquid crystal phase) showing a polarizing microscope texture of a phase in a high-temperature range adjacent to the crystal phase.
Figure 4:
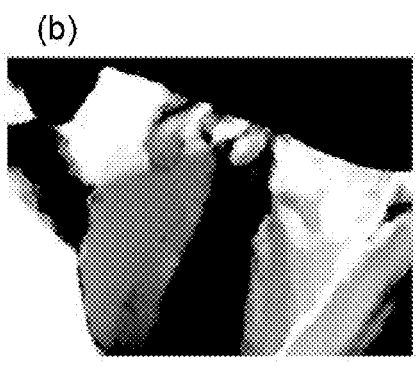
Figure 5:
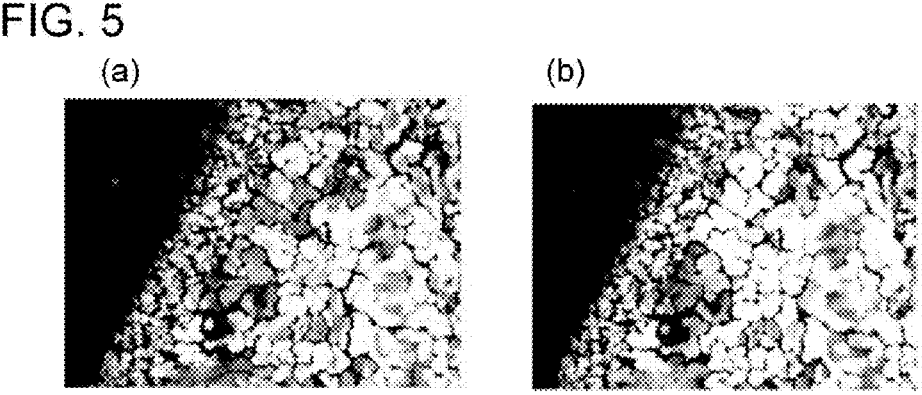
FIG. 5 includes (a) an example of a polarizing microscope photograph (crystal phase) showing a polarizing microscope texture at room temperature of compound d obtained in Example 4, and (b) an example of a polarizing microscope photograph (high-order liquid crystal phase) showing a polarizing microscope texture of a phase in a high-temperature range adjacent to the crystal phase.
Figure 6:
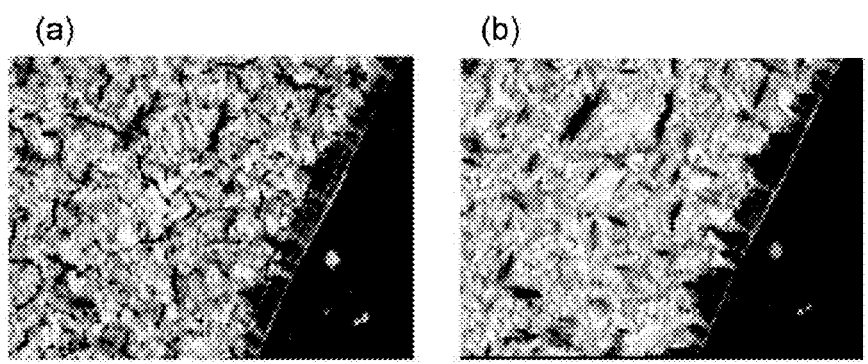
FIG. 6 includes (a) an example of a polarizing microscope photograph (crystal phase) showing a polarizing microscope texture at room temperature of compound e obtained in Example 5, and (b) an example of a polarizing microscope photograph (high-order liquid crystal phase) showing a polarizing microscope texture of a phase in a high-temperature range adjacent to the crystal phase.
Figure 7:
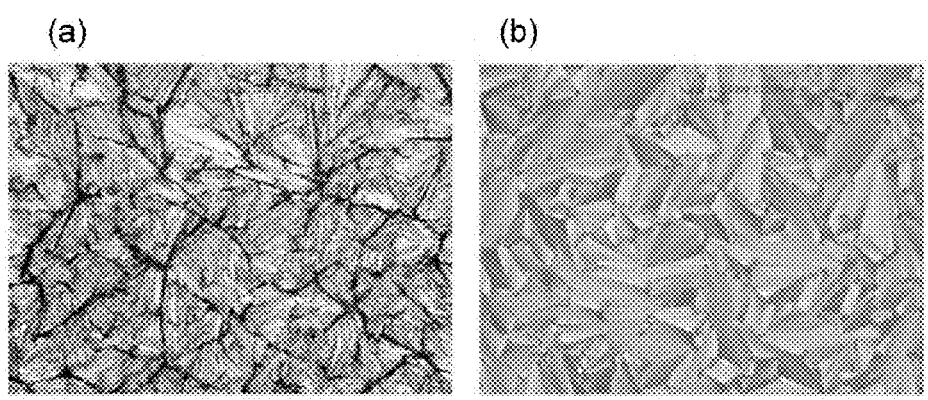
FIG. 7 includes (a) an example of a polarizing microscope photograph (crystal phase) showing a polarizing microscope texture at room temperature of compound f obtained in Example 6, and (b) an example of a polarizing microscope photograph (high-order liquid crystal phase) showing a polarizing microscope texture of a phase in a high-temperature range adjacent to the crystal phase.
Figure 8:
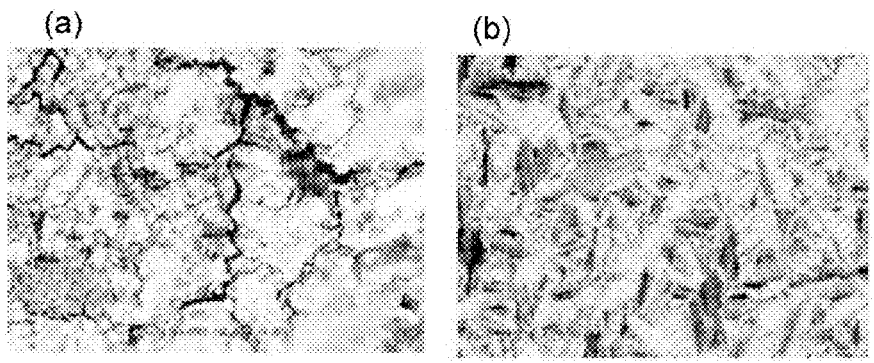
FIG. 8 includes (a) an example of a polarizing microscope photograph (crystal phase) showing a polarizing microscope texture at room temperature of compound g obtained in Example 7, and (b) an example of a polarizing microscope photograph (high-order liquid crystal phase) showing a polarizing microscope texture of a phase in a high-temperature range adjacent to the crystal phase.
Figure 9:
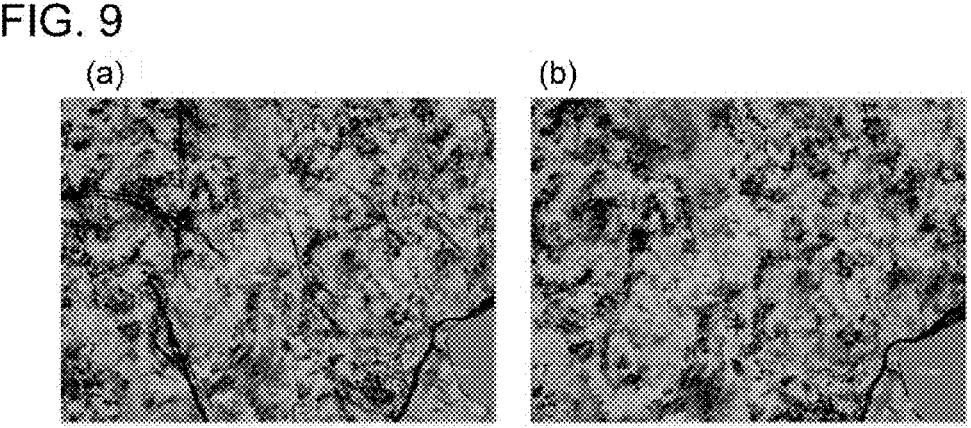
FIG. 9 includes (a) an example of a polarizing microscope photograph (crystal phase) showing a polarizing microscope texture at room temperature of compound h obtained in Example 8, and (b) an example of a polarizing microscope photograph (high-order liquid crystal phase) Snowing a polarizing microscope: texture of a phase in a high-temperature range adjacent to the crystal phase.
Figure 10:
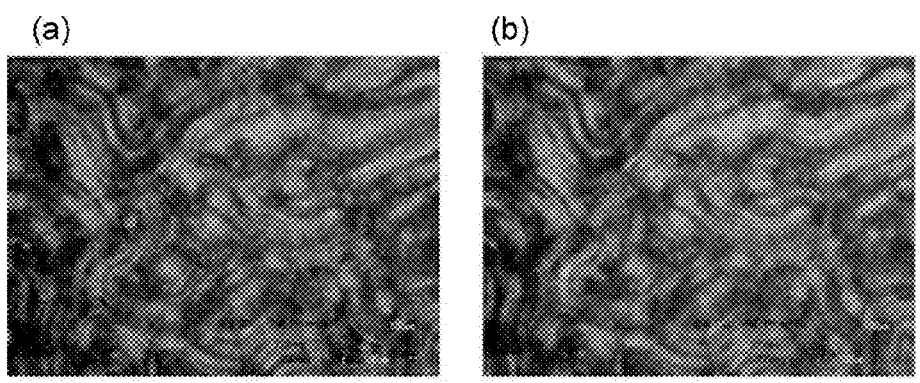
FIG. 10 includes (a) an example of a polarizing microscope photograph (crystal phase) showing a polarizing microscope texture at room temperature of compound i obtained in Example 9, and (b) an example of a polarizing microscope photograph (high-order liquid, crystal phase) showing a polarizing microscope texture of a phase in a high-temperature range adjacent to the crystal phase.
Figure 11:
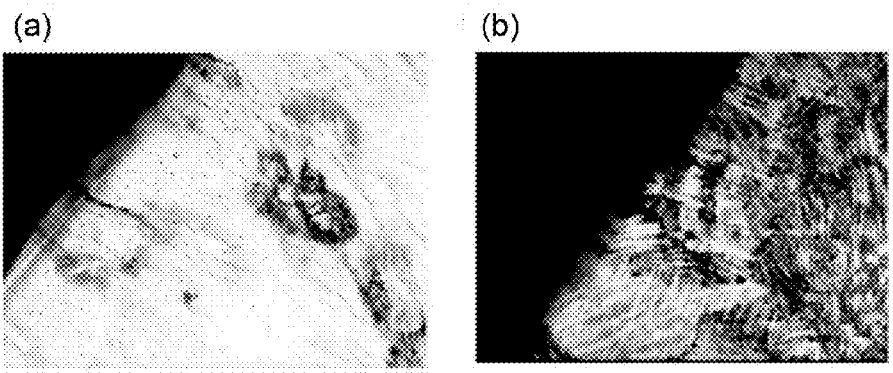
FIG. 11 includes (a) an example of a polarizing microscope photograph (crystal phase) showing a polarizing microscope texture at room, temperature of compound j obtained in Example 10, and (b) an example of a polarizing microscope photograph (high-order liquid crystal phase) showing a polarizing microscope texture of a phase in a high-temperature range adjacent to the crystal phase.
Figure 12:
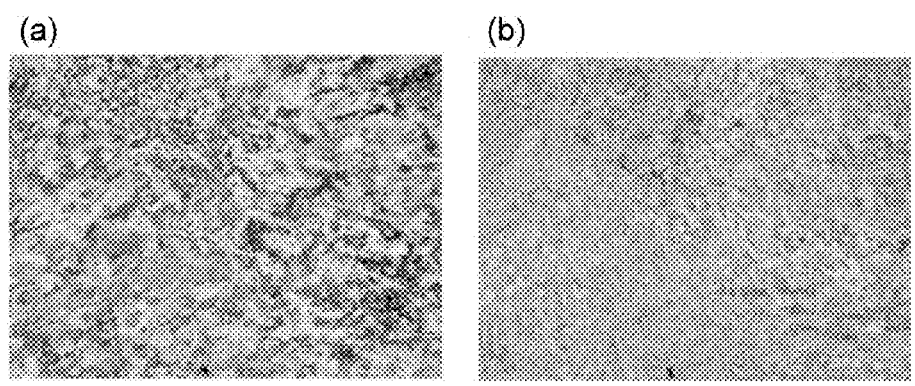
FIG. 12 includes (a) an example of a polarizing microscope photograph (crystal phase) showing a polarizing microscope texture at room temperature of compound k obtained in Example 11, and (b) an example of a polarizing microscope photograph (high-order liquid crystal phase) showing a polarizing microscope texture of a phase in a high-temperature range adjacent to the crystal phase.
Figure 13:
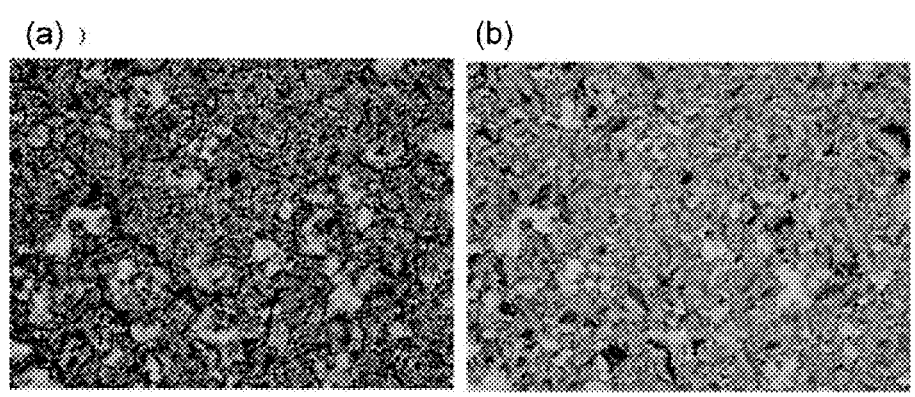
FIG. 13 includes (a) an example of a polarizing microscope photograph (crystal phase) showing a polarizing microscope texture at room temperature of compound 1 obtained in Example 12, and (b) an example of a polarizing microscope photograph (high-order liquid crystal phase) showing a polarizing microscope texture of a phase in a high-temperature range adjacent to the crystal phase.
Figure 14:
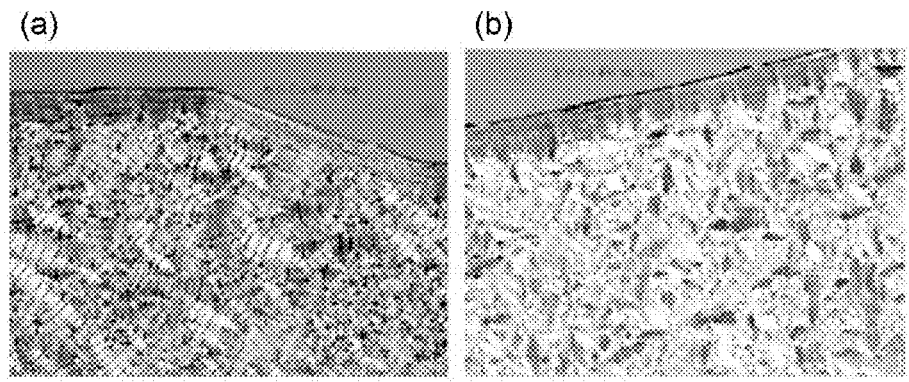
FIG. 14 includes (a) an example of a polarizing microscope photograph (crystal phase) showing a polarizing microscope texture at room temperature of compound m obtained in Example 13, and (b) an example of a polarizing microscope photograph (high-order liquid crystal phase) showing a polarizing microscope texture of a phase in a high-temperature range adjacent to the crystal phase.
Figure 15:
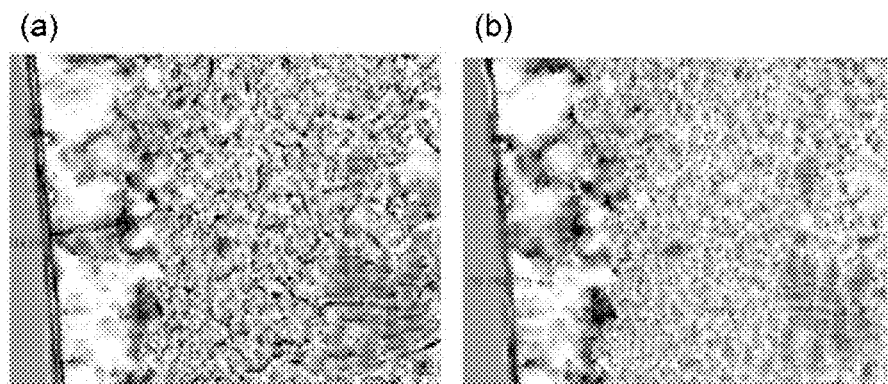
FIG. 15 includes (a) an example of a polarizing microscope photograph (crystal phase) showing a polarizing microscope texture at room temperature of compound n obtained in Example 14, and (b) an example of a polarizing microscope photograph (high-order liquid crystal phase) showing a polarizing microscope texture of a phase in a high-temperature range adjacent to the crystal phase.
Figure 16:
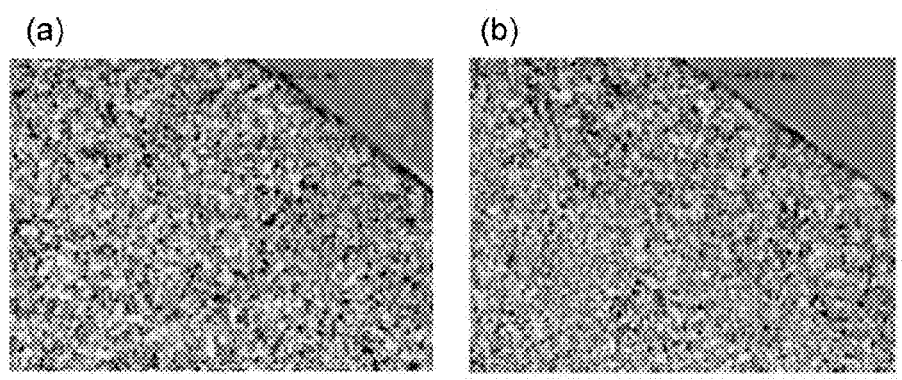
FIG. 16 includes (a) an example of a polarizing microscope photograph (crystal phase) showing a polarizing microscope texture at room temperature of compound o obtained in Example 15, and (b) an example of a polarizing microscope photograph (high-order liquid crystal phase) showing a polarizing microscope texture of a phase in a high-temperature range adjacent to the crystal phase.
Figure 17:
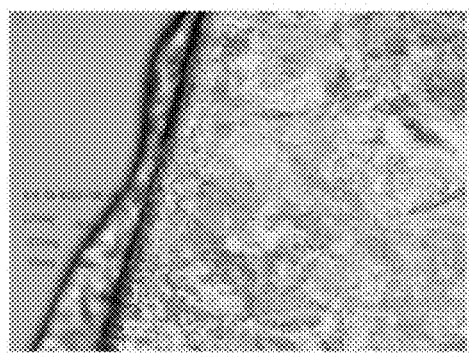
FIG. 17 includes (a) an example of a polarizing microscope photograph (crystal phase) showing a polarizing microscope texture at room temperature of compound p obtained in Example 16, and (b) an example of a polarizing microscope photograph (high-order liquid crystal phase) showing a polarizing microscope texture of a phase in a high-temperature range adjacent to the crystal phase.
Figure 17:
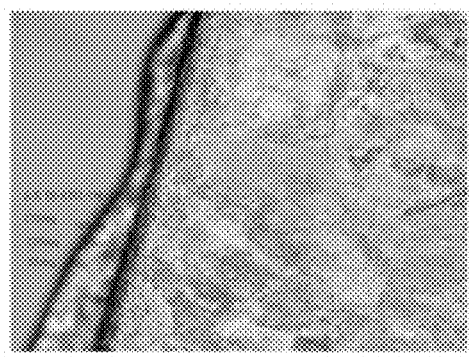
Figure 18:
FIG. 18 includes (a) an example of a polarizing microscope photograph (crystal phase) showing a polarizing microscope texture at room temperature of compound q obtained in Example 17, and (b) an example of a polarizing microscope photograph (high-order liquid crystal phase) showing a polarizing microscope texture of a phase in a high-temperature range adjacent to the crystal phase.
Figure 18:
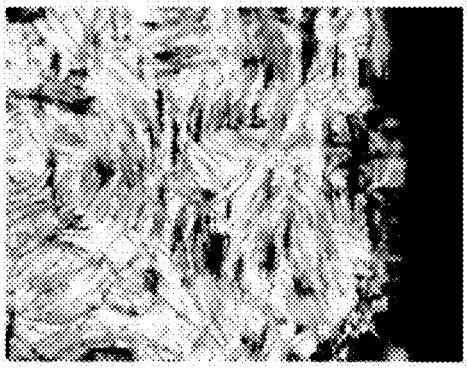
Figure 19:
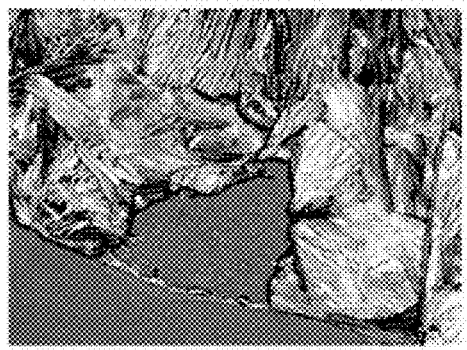
FIG. 19 includes (a) an example of a polarizing microscope photograph (crystal phase) showing a polarizing microscope texture at room temperature of compound r obtained in Example 18, and (b) an example of a polarizing microscope photograph (high-order liquid crystal phase) showing a polarizing microscope texture of a phase in a high-temperature range adjacent to the crystal phase.
Figure 19:
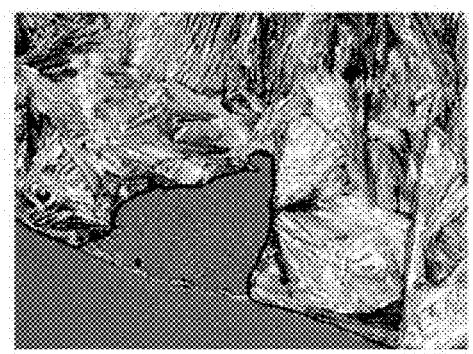
Figure 20:
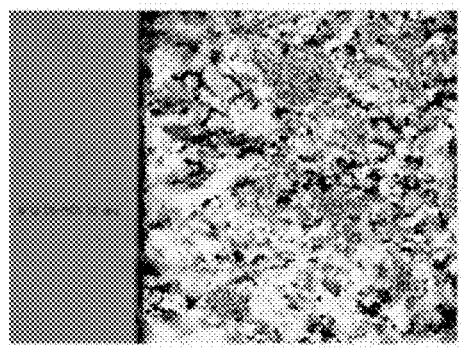
FIG. 20 includes (a) an example of a polarizing microscope photograph (crystal phase) showing a polarizing microscope texture at room temperature of compound s obtained in Example 19, and (b) an example of a polarizing microscope photograph (high-order liquid crystal phase) showing a polarizing microscope texture of a phase in a high-temperature range adjacent to the crystal phase.
Figure 20:
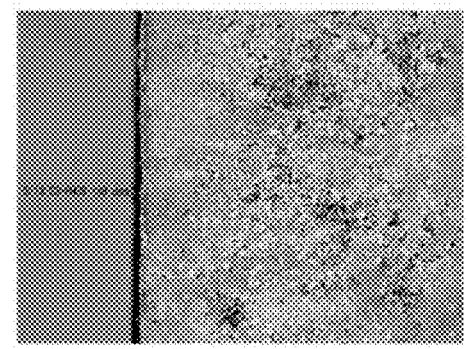
Figure 21:
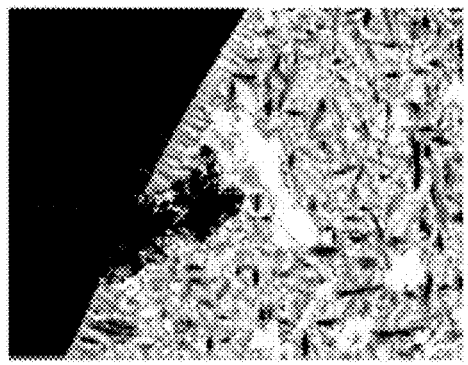
FIG. 21 includes (a) an example of a polarizing microscope photograph (crystal phase) showing a polarizing microscope texture at room temperature of compound t obtained in Example 20, and (b) an example of a polarizing microscope photograph (high-order liquid crystal phase) showing a polarizing microscope texture of a phase in a high-temperature range adjacent to the crystal phase.
Figure 21:
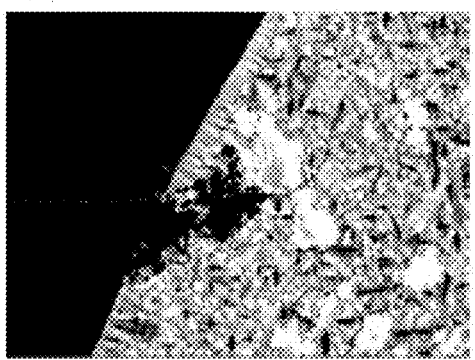
Figure 22:
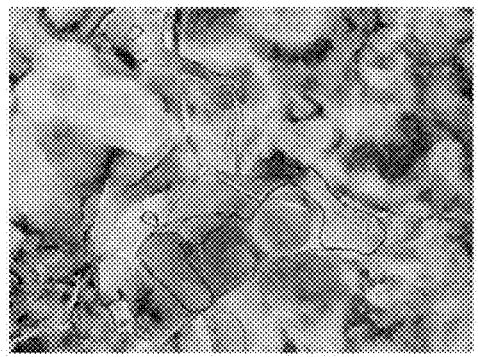
FIG. 22 includes (a) an example of a polarizing microscope photograph (crystal phase) showing a polarizing microscope texture at room temperature of compound u obtained in Example 21, and (b) an example of a polarizing microscope photograph (high-order liquid crystal phase) showing a polarizing microscope texture of a phase in a high-temperature range adjacent to the crystal phase.
Figure 22:
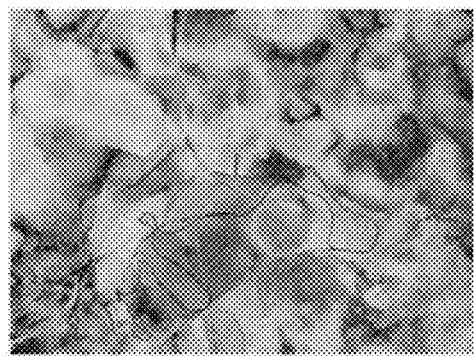
Figure 23:
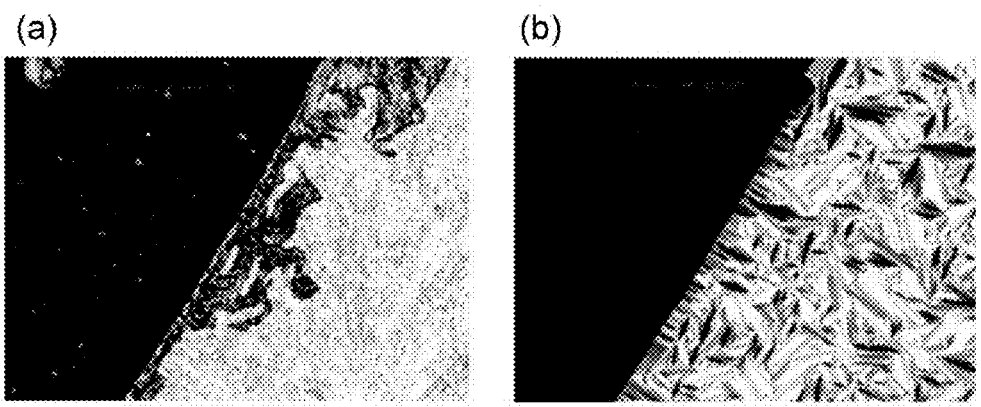
FIG. 23 includes (a) an example of a polarizing microscope photograph (crystal phase) showing a polarizing microscope texture at room temperature of compound v obtained in Example 22, and (b) an example of a polarizing microscope photograph (high-order liquid crystal phase) showing a polarizing microscope texture of a phase in a high-temperature range adjacent to the crystal phase.

| Example | Organic semiconductor material | Figure number of observation of liquid crystal phase | Transistor evaluation results | | |
|---|---|---|---|---|---|
| | | | Mobility (cm²/Vs) | Error of mobility | On/Off ratio |
| Example 23 | Compound a | FIG. 2 | 0.75 | ±12% | $6.0 \times 10^6$ |
| Example 24 | Compound b | FIG. 3 | 1.32 | ±18% | $5.5 \times 10^5$ |
| Example 25 | Compound c | FIG. 4 | 0.35 | ±21% | $1.0 \times 10^6$ |
| Example 26 | Compound d | FIG. 5 | 0.20 | ±25% | $4.0 \times 10^5$ |
| Example 27 | Compound e | FIG. 6 | 0.38 | ±18% | $2.0 \times 10^6$ |
| Example 28 | Compound f | FIG. 7 | 0.27 | ±22% | $5.0 \times 10^5$ |
| Example 29 | Compound g | FIG. 8 | 0.79 | ±19% | $1.0 \times 10^6$ |
| Example 30 | Compound h | FIG. 9 | 0.48 | ±17% | $8.0 \times 10^5$ |
| Example 31 | Compound i | FIG. 10 | 0.32 | ±22% | $7.0 \times 10^5$ |
| Example 32 | Compound j | FIG. 11 | 3.08 | ±21% | $1.0 \times 10^6$ |
| Example 33 | Compound k | FIG. 12 | 1.10 | ±23% | $1.0 \times 10^6$ |
| Example 34 | Compound l | FIG. 13 | 0.33 | ±18% | $6.5 \times 10^5$ |
| Example 35 | Compound m | FIG. 14 | 0.95 | ±17% | $7.0 \times 10^5$ |
| Example 36 | Compound n | FIG. 15 | 0.45 | ±20% | $5.5 \times 10^5$ |
| Example 37 | Compound o | FIG. 16 | 1.23 | ±19% | $2.0 \times 10^6$ |
| Example 38 | Compound p | FIG. 17 | 0.95 | ±23% | $8.0 \times 10^5$ |
| Example 39 | Compound q | FIG. 18 | 0.51 | ±18% | $1.0 \times 10^6$ |
| Example 40 | Compound r | FIG. 19 | 0.99 | ±20% | $1.0 \times 10^6$ |
| Example 41 | Compound s | FIG. 20 | 2.96 | ±22% | $9.0 \times 10^5$ |
| Example 42 | Compound t | FIG. 21 | 0.43 | ±18% | $7.0 \times 10^6$ |
| Example 43 | Compound u | FIG. 22 | 0.25 | ±25% | $4.5 \times 10^5$ |
| Example 44 | Compound v | FIG. 23 | 0.32 | ±21% | $7.5 \times 10^5$ |
| Comparative Exmple 1 | Comparative Example 1 | — | 0.11 | ±54% | $1.0 \times 10^6$ |
| Comparative Example 2 | Comparative Example 2 | — | 0.06 | ±45% | $3.0 \times 10^5$ |

Referring to the results shown Table 1 and FIGS. 2 to 23, the organic semiconductor materials of the present invention exhibit a high-order liquid crystal phase, and thus provide transistor elements which have a practical mobility and in which the variation in mobility is small. In contrast, the compounds of Comparative Examples do not exhibit a high-order liquid crystal phase. The mobility of the resulting transistor characteristics is low, and the error of mobility is large.

INDUSTRIAL APPLICABILITY

The compound of the present invention can be used as an organic semiconductor, and can be used in an organic transistor in which the organic semiconductor material, is used as an organic semiconductor layer.

REFERENCE SIGNS LIST 1. substrate
2. gate electrode
3. gate insulating film
4. organic semiconductor
5. source electrode
6. drain electrode

The invention claimed is:
1. A benzothienobenzothiophene derivative represented by general formula (1),

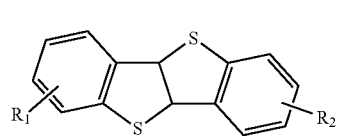 (1)

In the formula, R$_1$— is (I) below and R$_2$— is (II) below:
(I) A group represented by general formula (2) or (3):

 (2)

 (3)

where Ar$_1$ represents an aromatic hydrocarbon group or heteroaromatic group which may have a substituent, Ar$_2$ represents an aromatic hydrocarbon group which may have a substituent or a heteroaromatic group which may have a substituent, and R' represents a hydrogen atom, a trialkylsilyl group having an alkyl group having 1 to 4 carbon atoms, an alkyl group having 1 to 20 carbon atoms, or an aromatic hydrocarbon group or heteroaromatic group which may have a substituent;
(II) A group selected from
an alkyl group having 2 to 20 carbon atoms, an alkenyl group having 2 to 20 carbon atoms, an alkyl group having a halogen atom and 2 to 20 carbon atoms, an alkoxyalkyl group having 3 to 20 carbon atoms, an alkylsulfanylalkyl group having 3 to 20 carbon atoms, an alkylaminoalkyl group having 3 to 20 carbon atoms, an aromatic hydrocarbon group or heteroaromatic group, and
an aromatic hydrocarbon group or heteroaromatic group having, as a substituent, an alkyl group having 1 to 20 carbon atoms, an alkenyl group having 2 to 20 carbon atoms, an alkyl group having a halogen atom and 1 to 20 carbon atoms, an alkoxyalkyl group having 3 to 20 carbon atoms, an alkylsulfanylalkyl group having 3 to 20 carbon atoms, or an alkylaminoalkyl group having 3 to 20 carbon atoms.

2. The benzothienobenzothiophene derivative according to claim 1, represented by general formula (4) below.

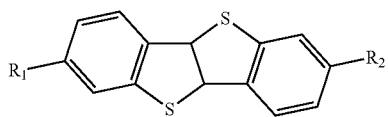
(4)

(In the formula, $R_1$— is a group represented by general formula (2) or (3) below:

(2)

(3)

(where $Ar_1$, $Ar_e$, and R' represent the same as the above, and $R_2$— is a group selected from an alkyl group having 2 to 20 carbon atoms, an alkenyl group having 2 to 20 carbon atoms, an alkyl group having a halogen atom and 2 to 20 carbon atoms, an alkoxyalkyl group having 3 to 20 carbon atoms, an alkylsulfanylalkyl group having 3 to 20 carbon atoms, an alkylaminoalkyl group having 3 to 20 carbon atoms, an aromatic hydrocarbon group or heteroaromatic group, and an aromatic hydrocarbon group or heteroaromatic group having, as a substituent, an alkyl group having 1 to 20 carbon atoms, an alkenyl group having 2 to 20 carbon atoms, an alkyl group having a halogen atom and 1 to 20 carbon atoms, an alkoxyalkyl group having 3 to 20 carbon atoms, an alkylsulfanylalkyl group having 3 to 20 carbon atoms, or an alkylaminoalkyl group having 3 to 20 carbon atoms.

3. An organic semiconductor material comprising the benzothienobenzothiophene derivative according to claim 1.

4. An organic semiconductor ink comprising the organic semiconductor material according to claim 3.

5. An organic semiconductor film comprising the organic semiconductor material according to claim 3.

6. An organic semiconductor device comprising the organic semiconductor material according to claim 3.

7. An organic transistor comprising the organic semiconductor material according to claim 3 as an organic semiconductor layer.

* * * * *